United States Patent
Enomoto

(10) Patent No.: US 8,393,789 B2
(45) Date of Patent: Mar. 12, 2013

(54) RADIOGRAPHIC IMAGE CAPTURE MANAGING SYSTEM, AND RADIOGRAPHIC IMAGE CAPTURE MANAGING METHOD

(75) Inventor: Jun Enomoto, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 379 days.

(21) Appl. No.: 12/923,560

(22) Filed: Sep. 28, 2010

(65) Prior Publication Data

US 2011/0073769 A1    Mar. 31, 2011

(30) Foreign Application Priority Data

Sep. 29, 2009    (JP) ................................ 2009-225197

(51) Int. Cl.
*G01D 18/00* (2006.01)
(52) U.S. Cl. ...................................... 378/207; 378/116
(58) Field of Classification Search .................... 378/19, 378/98.8, 116, 207; 250/370.08, 370.09, 250/370.11
See application file for complete search history.

(56) References Cited

U.S. PATENT DOCUMENTS

| 7,032,132 | B2 | 4/2006 | Adachi |
| 7,138,636 | B2 | 11/2006 | Petrick et al. |
| 2008/0230708 | A1 | 9/2008 | Enomoto |
| 2009/0034990 | A1 | 2/2009 | Nakazato et al. |

FOREIGN PATENT DOCUMENTS

| JP | 2000-105297 | 4/2000 |
| JP | 2002-000592 | 1/2002 |
| JP | 2002-345802 | 12/2002 |
| JP | 2003-172783 | 6/2003 |
| JP | 2003-235836 | 8/2003 |
| JP | 3494683 | 11/2003 |
| JP | 2006-075387 | 3/2006 |
| JP | 2006-267101 | 10/2006 |
| JP | 2008-149151 | 7/2008 |
| JP | 2008-229102 | 10/2008 |
| JP | 2009-037141 | 2/2009 |
| JP | 2009-042361 | 2/2009 |

*Primary Examiner* — Courtney Thomas
(74) *Attorney, Agent, or Firm* — Jean C. Edwards, Esq.; Edwards Neils PLLC

(57) ABSTRACT

A radiographic image capture managing system includes an information storage unit for storing image information acquired by a radiation detector in chronological order, a usage status acquirer for acquiring information concerning a usage status of the radiation detector, a deterioration information acquirer for acquiring information concerning an extent of deterioration of the radiation detector based on the image information, a service life predictor for predicting a service life of the radiation detector based on the acquired information concerning the extent of deterioration and the acquired information concerning the usage status, a service life prolongation information setter for setting service life prolongation advice information required to prolong the predicted service life based on a preset relationship between the usage status and the extent of deterioration of the radiation detector and history information, and a service life prolongation advice output unit for transmitting service life prolongation advice information to at least a console.

14 Claims, 17 Drawing Sheets

230

RECORD 1
CASSETTE NUMBER
CONSOLE NUMBER
SERVICE LIFE
CHARACTERISTIC CURVE GRADIENT
LATEST ENVIRONMENTAL TEMPERATURE
LATEST TUBE VOLTAGE

RECORD 2
CASSETTE NUMBER
CONSOLE NUMBER
SERVICE LIFE
CHARACTERISTIC CURVE GRADIENT
LATEST ENVIRONMENTAL TEMPERATURE
LATEST TUBE VOLTAGE

FIG. 8A
234A

| | | |
|---|---|---|
| RECORD 1 | CASSETTE NUMBER / CONSOLE NUMBER / PROLONGED SERVICE LIFE ENVIRONMENTAL TEMPERATURE / PROLONGED SERVICE LIFE ENVIRONMENTAL TEMPERATURE | ... |
| RECORD 2 | CASSETTE NUMBER / CONSOLE NUMBER / PROLONGED SERVICE LIFE ENVIRONMENTAL TEMPERATURE / PROLONGED SERVICE LIFE ENVIRONMENTAL TEMPERATURE | ... |

FIG. 8B
234B

| | | |
|---|---|---|
| RECORD 1 | CASSETTE NUMBER / CONSOLE NUMBER / PROLONGED SERVICE LIFE TUBE VOLTAGE / PROLONGED SERVICE LIFE TUBE VOLTAGE | ... |
| RECORD 2 | CASSETTE NUMBER / CONSOLE NUMBER / PROLONGED SERVICE LIFE TUBE VOLTAGE / PROLONGED SERVICE LIFE TUBE VOLTAGE | ... |

RECORD 1
| CASSETTE NUMBER |
| CONSOLE NUMBER |
| DATE (SERVICE LIFE PREDICTION) |

RECORD 2
| CASSETTE NUMBER |
| CONSOLE NUMBER |
| DATE (SERVICE LIFE PREDICTION) |

RECORD 3
| CASSETTE NUMBER |
| CONSOLE NUMBER |
| DATE (SERVICE LIFE PREDICTION) |

⋮

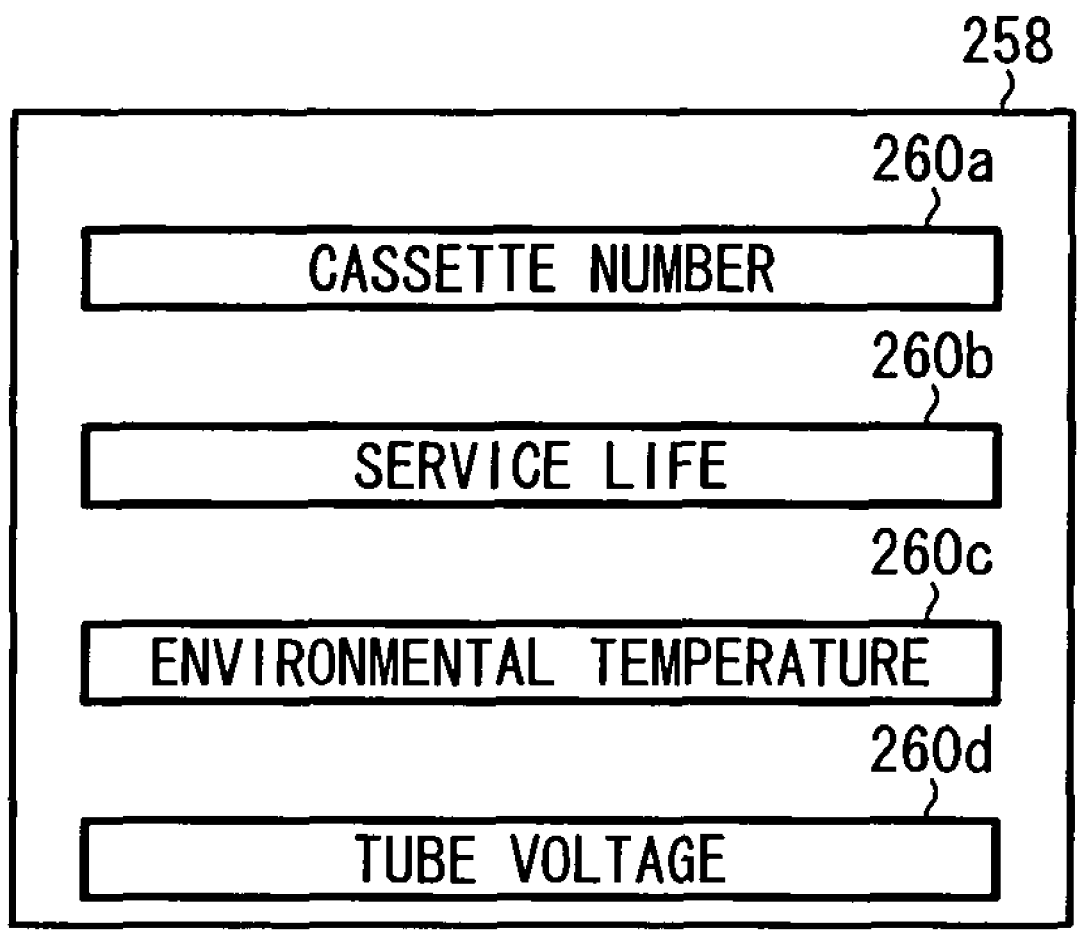

RADIOGRAPHIC IMAGE CAPTURE MANAGING SYSTEM, AND RADIOGRAPHIC IMAGE CAPTURE MANAGING METHOD

CROSS-REFERENCE TO RELATED APPLICATION

This application is based upon and claims the benefit of priority from Japanese Patent Application No. 2009-225197 filed on Sep. 29, 2009, of which the contents are incorporated herein by reference.

BACKGROUND OF THE INVENTION

1. Field of the Invention

The present invention relates to a radiographic image capture managing system and a radiographic image capture managing method, which are capable of remotely managing a radiation detecting apparatus used respectively in various radiographic image capturing chambers.

2. Description of the Related Art

In the medical field, there have widely been used radiation detecting apparatus that apply radiation to a subject and guide radiation that has passed through the subject to a radiation detector, which captures a radiographic image from the radiation. Known forms of radiation detectors include a conventional radiation film for recording a radiographic image by way of exposure, and a stimulable phosphor panel for storing radiation energy representing a radiographic image in a phosphor, and reproducing the radiographic image as stimulated light by applying stimulating light to the phosphor. The radiation film with the radiographic image recorded therein is supplied to a developing device in order to develop the radiographic image. Alternatively, the stimulable phosphor panel is supplied to a reading device in order to read the radiographic image as a visible image.

In an operating room or the like, it is necessary to read a recorded radiographic image immediately from a radiation conversion panel after the radiographic image has been captured for the purpose of quickly and appropriately treating the patient. As a radiation detector that meets such a requirement, radiation detecting apparatus have been developed having a solid-state detector for converting radiation directly into electric signals, or for converting visible light, which has been converted from radiation by a scintillator, into electric signals.

Conventional radiographic image capture managing systems, which are capable of remotely managing the above radiation detecting apparatus, are known from Japanese Laid-Open Patent Publication No. 2009-037141, Japanese Laid-Open Patent Publication No. 2009-042361, Japanese Laid-Open Patent Publication No. 2006-075387, Japanese Laid-Open Patent Publication No. 2002-000592, Japanese Laid-Open Patent Publication No. 2003-235836, Japanese Laid-Open Patent Publication No. 2006-267101, Japanese Laid-Open Patent Publication No. 2008-149151, Japanese Laid-Open Patent Publication No. 2003-172783, Japanese Laid-Open Patent Publication No. 2008-229102, and Japanese Laid-Open Patent Publication No. 2002-345802.

Japanese Laid-Open Patent Publication No. 2009-037141 discloses a method of determining whether or not there is a sign of failure of an image forming apparatus. More specifically, plural types of state data are received from the image forming apparatus and stored in a state database. Then, plural types of object data for determining a sign of failure are generated based on the plural types of state data. It is determined whether or not each of the plural types of object data is in excess of a reference value, and the determined results are weighted by weights set for the respective state data. Thereafter, it is determined whether or not there is a sign of failure of the image forming apparatus according to a majority rule.

Japanese Laid-Open Patent Publication No. 2009-042361 also discloses a method of determining whether or not there is a sign of failure of an image forming apparatus. More specifically, plural types of state data, which may be either values of control parameters of image forming apparatus, or detected data produced by a sensor and evaluation data generated based on the detected data, are stored in a database. Then, plural types of object data for determining a sign of failure are generated or extracted from the plural types of state data. It is determined whether or not each of the plural types of object data has a failure tendency, and the determined results are weighted by weights set for the respective state data. Thereafter, it is determined whether or not there is an overall sign of failure of the image forming apparatus according to a majority rule.

Japanese Laid-Open Patent Publication No. 2006-075387 discloses a method of managing a CT apparatus in a hospital from a remote location. For example, among maintenance data that is collected everyday from a hospital, data of a certain day of the week are sent to a service center once per week, and compared with plural types of past data from a week ago, a month ago, or three months ago. In this manner, long-term changes in the state of the CT apparatus can be tracked for a sign or possibility of failure of the image forming apparatus. If it is judged that there is a sign or possibility of failure of the image forming apparatus, then the service center requests a service station to dispatch a service staff member to the hospital. In response to the request, the service station dispatches a service staff member to the hospital, and the dispatched service staff member takes preventative action before the image forming apparatus actually fails. Conversely, if it is judged that a sign or possibility of failure of the image forming apparatus does not exist, then the service center continues to monitor the maintenance data that are periodically received from the hospital. According to Japanese Laid-Open Patent Publication No. 2006-075387, the service center can grasp an actual failure of the image forming apparatus or a sign of failure of the image forming apparatus remotely from the hospital, and can quickly request the service station to dispatch a service staff member to the hospital. Therefore, the service staff member can provisionally prepare equipment and replacement components required to repair the image forming apparatus, take them to the hospital, and promptly repair or otherwise perform maintenance on the image forming apparatus. Accordingly, downtime of the image forming apparatus can be eliminated or reduced. While the X-ray tube of the image forming apparatus warms up, maintenance data thereon are necessarily and routinely collected on days in which the CT apparatus is used. Therefore, the X-ray tube can be monitored for failures and time-dependent changes, without having to take the trouble to acquire such maintenance data again.

Japanese Laid-Open Patent Publication No. 2002-000592 reveals a self-diagnostic system for automatically diagnosing the operating status of an image capturing apparatus, which is connected by a communication means to a maintenance apparatus for performing maintenance on the image capturing apparatus. The image capturing apparatus includes a self-diagnostic means for automatically diagnosing the operating status of the image capturing apparatus, an amount-of-information measuring means for measuring the size of information to be exchanged between the image capturing apparatus and the maintenance apparatus, and an information compressing means for compressing the exchanged information. The information compressing means compresses the exchanged information depending on an output signal output from the amount-of-information, measuring means.

Japanese Laid-Open Patent Publication No. 2003-235836 discloses a reproducibility test service apparatus. In order to reproduce past operations of a medical system, a plurality of past log files directly or indirectly provided by the medical system are stored in a storage device, and a plurality of past operations of the medical system are reproduced on a pseudo-X-ray CT system based on the log files that are stored in the storage device.

Japanese Laid-Open Patent Publication No. 2006-267101 discloses a semiconductor X-ray detector. The disclosed semiconductor X-ray detector has a planar area subjected to X-ray exposure, which is simulated based on an adjustment bias of the semiconductor X-ray detector, to produce a gain image of the semiconductor X-ray detector. The gain image is used in order to calibrate the semiconductor X-ray detector when an X-ray beam is not projected onto the semiconductor X-ray detector. The publication states that the gain image is remotely managed.

Japanese Laid-Open Patent Publication No. 2008-149151 discloses a maintenance assistance information managing apparatus, which is connected to a medical system and a maintenance service apparatus by an electronic communications circuit. The maintenance assistance information managing apparatus includes a unit configured to receive plural log files representing operational records from the medical system, a unit configured to store the log files, a unit configured to analyze the stored log files and determine a usage frequency for each operation type, and a unit configured to provide usage frequency or information derived therefrom in response to a request from the maintenance service apparatus. The maintenance assistance information managing apparatus can identify the cause of a failure in the medical system in a short period of time, thereby reducing the failure period or system downtime.

Japanese Laid-Open Patent Publication No. 2003-172783 discloses a system for detecting a new image defect produced on an image capturing panel, issuing a warning concerning the detected new image defect, and removing radiographic image information that causes the image defect.

Japanese Laid-Open Patent Publication No. 2008-229102 discloses that a warning is issued when an area is detected including a succession of pixel defects of a radiation solid-state detector over a certain number of pixels.

Japanese Laid-Open Patent Publication No. 2002-345802 discloses that replacement component information obtained by a replacement component information acquiring means of a medical image generating apparatus is displayed, in order to allow a user to know which component needs to be replaced and a time at which the component should be replaced.

The related art documents referred to above disclose systems and methods for predicting failures from history information of the apparatus and state information such as image data, monitoring of failures and time-dependent changes, and indicating a time at which to replace a component. However, the related art do not disclose or provide advice concerning ways to extend the service life of radiation detecting apparatus and times at which to replace components thereof. The systems and methods according to the related art also are problematic in that they cannot increase the efficiency with which radiation detecting apparatus are used, and cannot lower running costs.

SUMMARY OF THE INVENTION

It is an object of the present invention to provide a radiographic image capture managing system and a radiographic image capture managing method, which can remotely manage radiation detecting apparatus used respectively in various radiographic image capturing chambers, so as to predict and indicate the service life of radiation detecting apparatus based on the present usage status thereof, and which can produce advice enabling prolongation of the service life of such radiation detecting apparatus, for thereby increasing the efficiency with which the radiation detecting apparatus are used, and lowering running costs of such radiation detecting apparatus.

According to the present invention, there is provided a radiographic image capture managing system comprising at least one radiographic image capturing system including a radiation source, a radiation detector for detecting radiation emitted from the radiation source and transmitted through a subject and converting the detected radiation into radiographic image information, and a controller for controlling at least the radiation source and the radiation detector, and a manager for managing the at least one radiographic image capturing system. The manager comprises an information storage unit for storing at least one item of image information acquired by the radiation detector in chronological order, a usage status acquirer for acquiring information concerning a usage status of the radiation detector, a deterioration information acquirer for acquiring information concerning an extent of deterioration of the radiation detector based on the at least one item of image information stored in the information storage unit, a service life predictor for predicting a service life of the radiation detector based on the acquired information concerning the extent of deterioration of the radiation detector and the acquired information concerning the usage status of the radiation detector, a service life prolongation information setter for setting information concerning a new usage status required to prolong the predicted service life based on a preset relationship between the usage status and deterioration of the radiation detector and the acquired information concerning the usage status of the radiation detector, and a service life prolongation advice output unit for transmitting the information concerning the new usage status as service life prolongation advice information to at least the controller.

The image information stored in the information storage unit may comprise radiographic image information.

The manager may further comprise an offset image acquirer for reading a dark current of the radiation detector and acquiring offset image information from the read dark current. The image information stored in the information storage unit may comprise the offset image information.

The information concerning the extent of deterioration of the radiation detector may comprise at least a size (number of pixels) of a pixel defect.

The information concerning the usage status may comprise an environmental temperature of the radiation detector.

The usage status acquirer may acquire information concerning the usage status of the radiation detector from a history of temperature information produced by a thermometer associated with the radiation detector.

The information concerning the usage status may comprise a dose of radiation applied to the radiation detector.

The usage status acquirer may acquire information concerning the usage status of the radiation detector from a history of tube voltages set in the radiation source.

A processing sequence may be periodically performed over at least the usage status acquirer, the deterioration information acquirer, the service life predictor, the service life prolongation information setter, and the service life prolongation advice output unit.

Alternatively, a processing sequence may be periodically performed over at least the usage status acquirer, the deterioration information acquirer, and the service life predictor, and after the processing sequence over the usage status acquirer, the deterioration information acquirer, and the service life predictor is performed a plurality of times, the service life prolongation information setter and the service life prolongation advice output unit may perform processes thereof.

Alternatively, a processing sequence may be periodically performed over at least the usage status acquirer, the deterioration information acquirer, and the service life predictor, and when a time representing the predicted service life falls within a threshold value, the service life prolongation information setter and the service life prolongation advice output unit may perform processes thereof.

The processing sequence may be periodically performed at time intervals that are changed depending on the extent of deterioration of the radiation detector.

The processing sequence may be periodically performed at time intervals that are made shorter when a time representing the predicted service life falls within a threshold value.

According to the present invention, there is further provided a radiographic image capture managing method for managing at least one radiographic image capturing system including a radiation source, a radiation detector for detecting radiation emitted from the radiation source and transmitted through a subject and converting the detected radiation into radiographic image information, and a controller for controlling at least the radiation source and the radiation detector, comprising the steps of storing at least one item of image information acquired by the radiation detector in an information storage unit in chronological order, acquiring information concerning a usage status of the radiation detector, acquiring information concerning an extent of deterioration of the radiation detector based on the at least one item of image information stored in the information storage unit, predicting a service life of the radiation detector based on the acquired information concerning the extent of deterioration of the radiation detector and the acquired information concerning the usage status of the radiation detector, setting information concerning a new usage status required to prolong the predicted service life based on a preset relationship between the usage status and deterioration of the radiation detector and the acquired information concerning the usage status of the radiation detector, and transmitting the information concerning the new usage status as service life prolongation advice information to at least the controller.

The radiographic image capture managing system and the radiographic image capture managing method according to the present invention are capable of remotely managing radiation detectors installed in respective radiographic image capturing chambers, and also of predicting and indicating the service life of radiation detectors based on the present usage status thereof, and producing advice for prolonging the service life of such radiation detectors. As a result, the efficiency with which the radiation detectors can be used is increased, thereby resulting in a reduction in running costs at the radiographic image capturing chambers.

The above and other objects, features, and advantages of the present invention will become more apparent from the following description when taken in conjunction with the accompanying drawings in which preferred embodiments of the present invention are shown by way of illustrative example.

BRIEF DESCRIPTION OF THE DRAWINGS

FIG. 8A is a diagram showing by way of example contents of a first service life information table;

FIG. 8B is a diagram showing by way of example contents of a second service life information table;

FIG. 9 is a diagram showing by way of example contents of a cassette information table;

FIG. 11 is a diagram showing displayed items on a service life display image;

DESCRIPTION OF THE PREFERRED EMBODIMENTS

A radiographic image capture managing system, a radiographic image capture managing method, and a mobile radiographic image capturing apparatus according to preferred embodiments of the present invention will be described below with reference to FIGS. 1 through 17.

Figure 1:
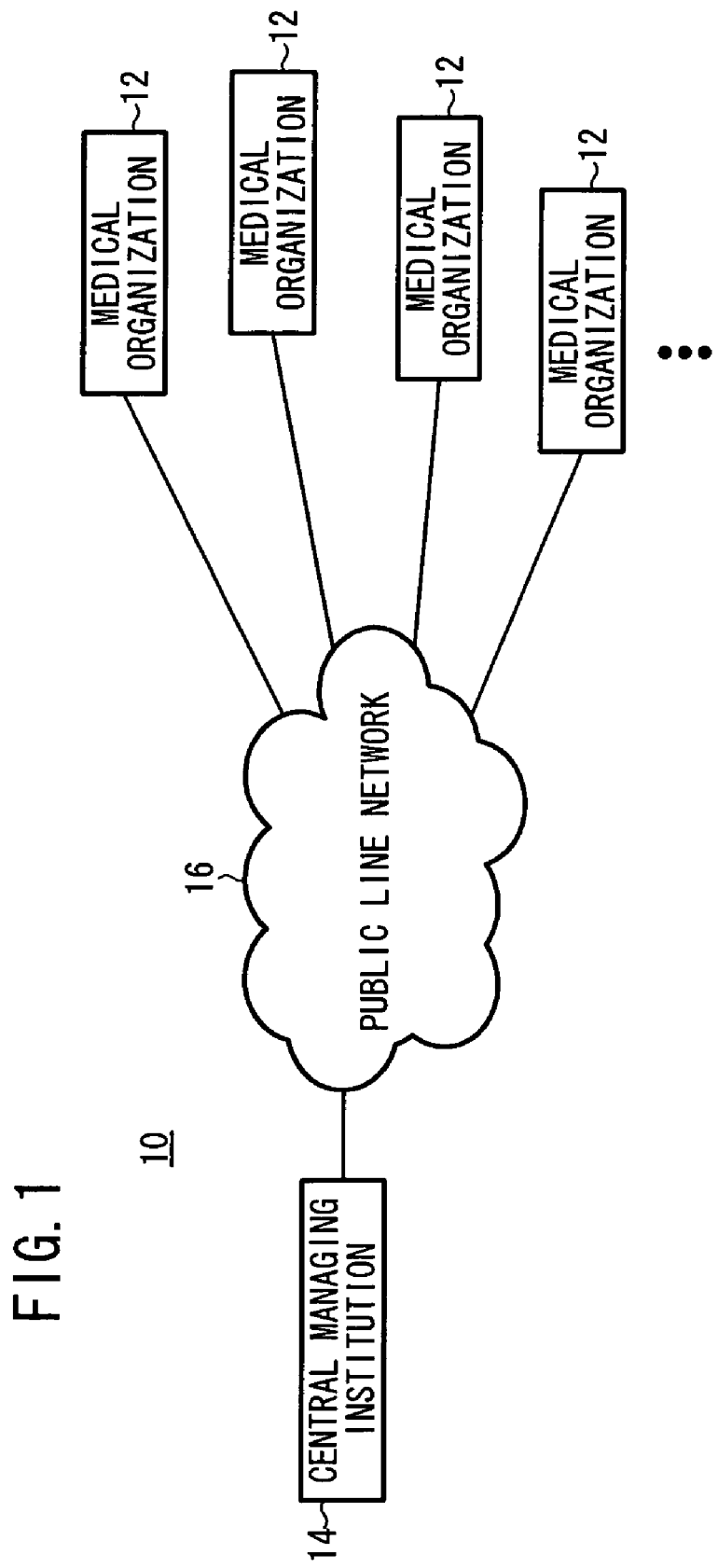
FIG. 1 is a block diagram of a radiographic image capture managing system according to an embodiment of the present invention.

As shown in FIG. 1, a radiographic image capture managing system 10 according to an embodiment of the present invention is made up of one or more medical organizations 12 (including doctor's offices, hospitals, and clinics, which are facilities where doctors, dentists, etc., perform medical practice) and an external central managing institution 14, which are connected to each other via a public line network 16.

Figure 2:
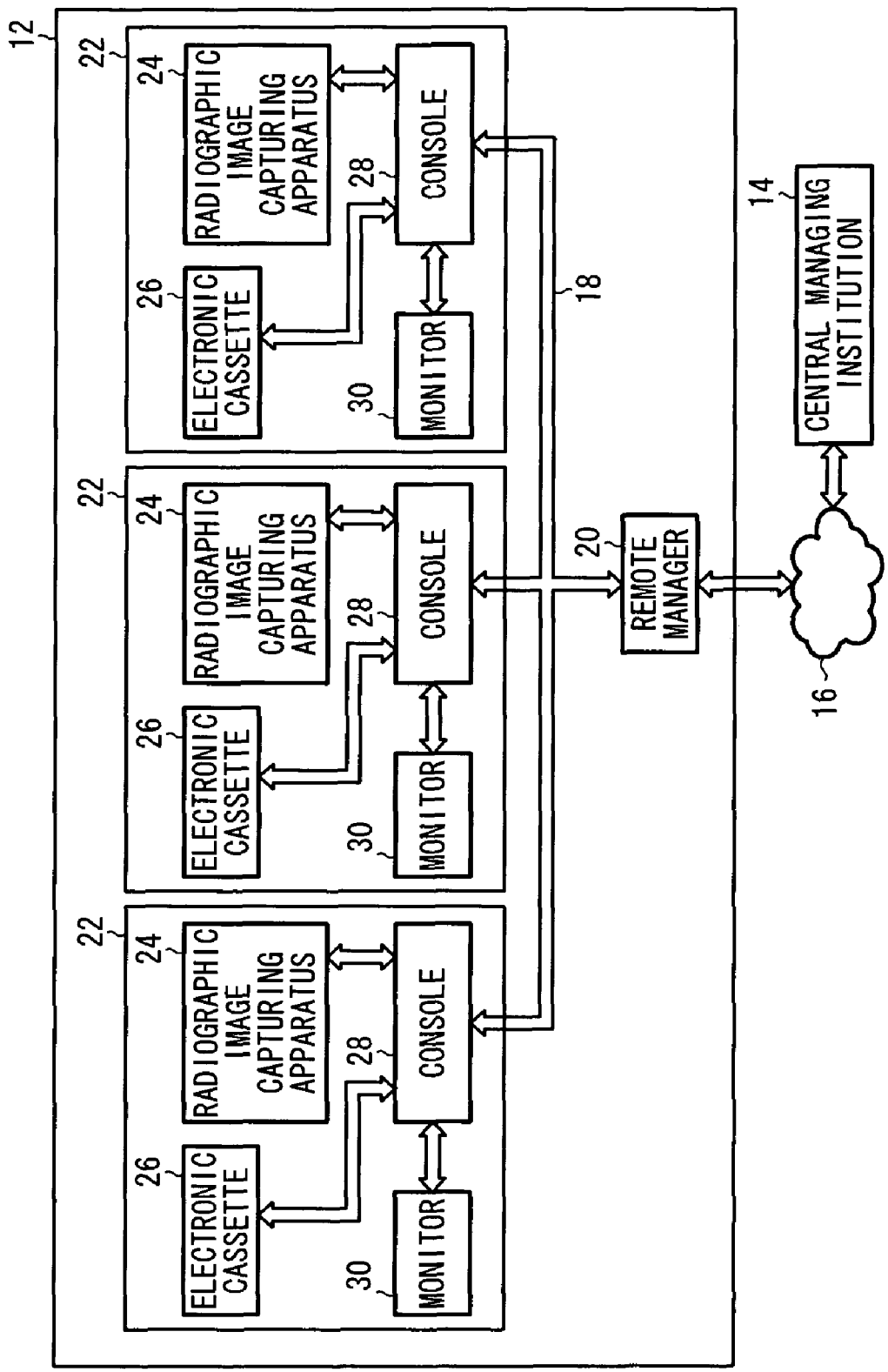
FIG. 2 is a block diagram of respective medical organizations, showing connections between a remote manager and consoles located in respective radiographic image capturing chambers.

As shown in FIG. 2, each of the medical organizations 12 includes a LAN (medical organization communication network) 18 used as an intranet, and a remote manager 20 connected between the LAN 18 and the public line network 16. The remote manager 20 is placed in a demilitarized zone, the security of which is increased by a firewall.

Each of the medical organizations 12 also includes at least one radiographic image capturing chamber 22 (three radiographic image capturing chambers 22 are shown in FIG. 2). The radiographic image capturing chamber 22 houses therein a radiation source, not shown, a radiographic image capturing apparatus 24 for capturing images of subjects in an upright position or a recumbent position, at least one radiation detecting apparatus (hereinafter referred to as an "electronic cassette") 26 of one or more types, and a console 28 for controlling the radiation source, the radiographic image capturing apparatus 24, and the electronic cassette 26. A display monitor 30 for confirming the radiographic image information, messages, and other information is connected to the console 28. Each of the medical organizations 12 also has at least one mobile radiographic image capturing apparatus (visiting car), not shown, which may be moved into a medical ward by a doctor or a radiological technician. The visiting car is capable of performing communications with the consoles 28 through a PHS line network, for example.

The radiographic image capturing apparatus 24 and the mobile radiographic image capturing apparatus have built-in or removable electronic cassettes 26 set therein, which can be replaced with new electronic cassettes 26 if the service life of the image capturing unit (radiation detector) thereof expires. Electronic cassettes 26 that are used as stand-alone electronic cassettes can also be replaced with new electronic cassettes 26.

Structural details of each of the electronic cassettes 26, i.e., the electronic cassettes 26 set in the radiographic image capturing apparatus 24, will be described below with reference to FIGS. 3 and 4.

Figure 3:
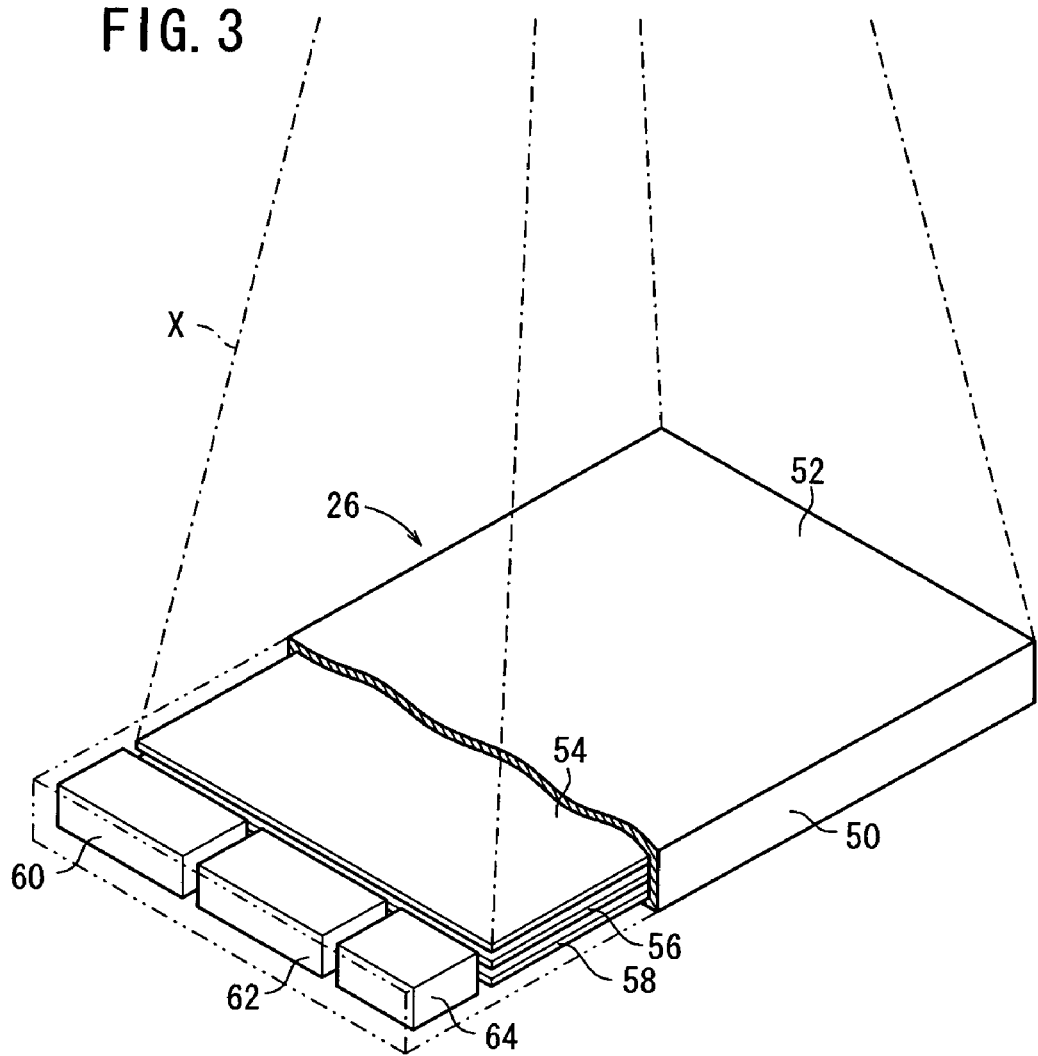
FIG. 3 is a perspective view, partially cut away, showing internal structural details of an electronic cassette.

As shown in FIG. 3, the electronic cassette 26 includes a casing 50 made of a material that is permeable to radiation X. The casing 50 houses therein a grid 54 for removing scattered rays of radiation X from a subject (patient), a radiation detector 56 for detecting radiation X that has passed through the subject, and a lead plate 58 for absorbing back scattered rays of radiation X, each of which are successively arranged in this order from an irradiated surface 52 of the casing 50 that is irradiated with radiation X. The irradiated surface 52 of the casing 50 may be constructed as the grid 54.

The casing 50 also houses therein a battery 60, which serves as a power supply for the electronic cassette 26, a cassette controller 62 for energizing the radiation detector 56 with electric power supplied from the battery 60, and a transceiver terminal 64 for sending and receiving information concerning the radiation X detected by the radiation detector 56, along with other various signals, to and from the console 28. The transceiver terminal 64 sends and receives such information and signals to and from the console 28 by way of wireless or wired communications.

A shield plate made of lead or the like should preferably be placed over at least the cassette controller 62 under the irradiated surface 52 of the casing 50 in order to protect the cassette controller 62 against damage, which would otherwise be caused if irradiated with radiation X.

Figure 4:
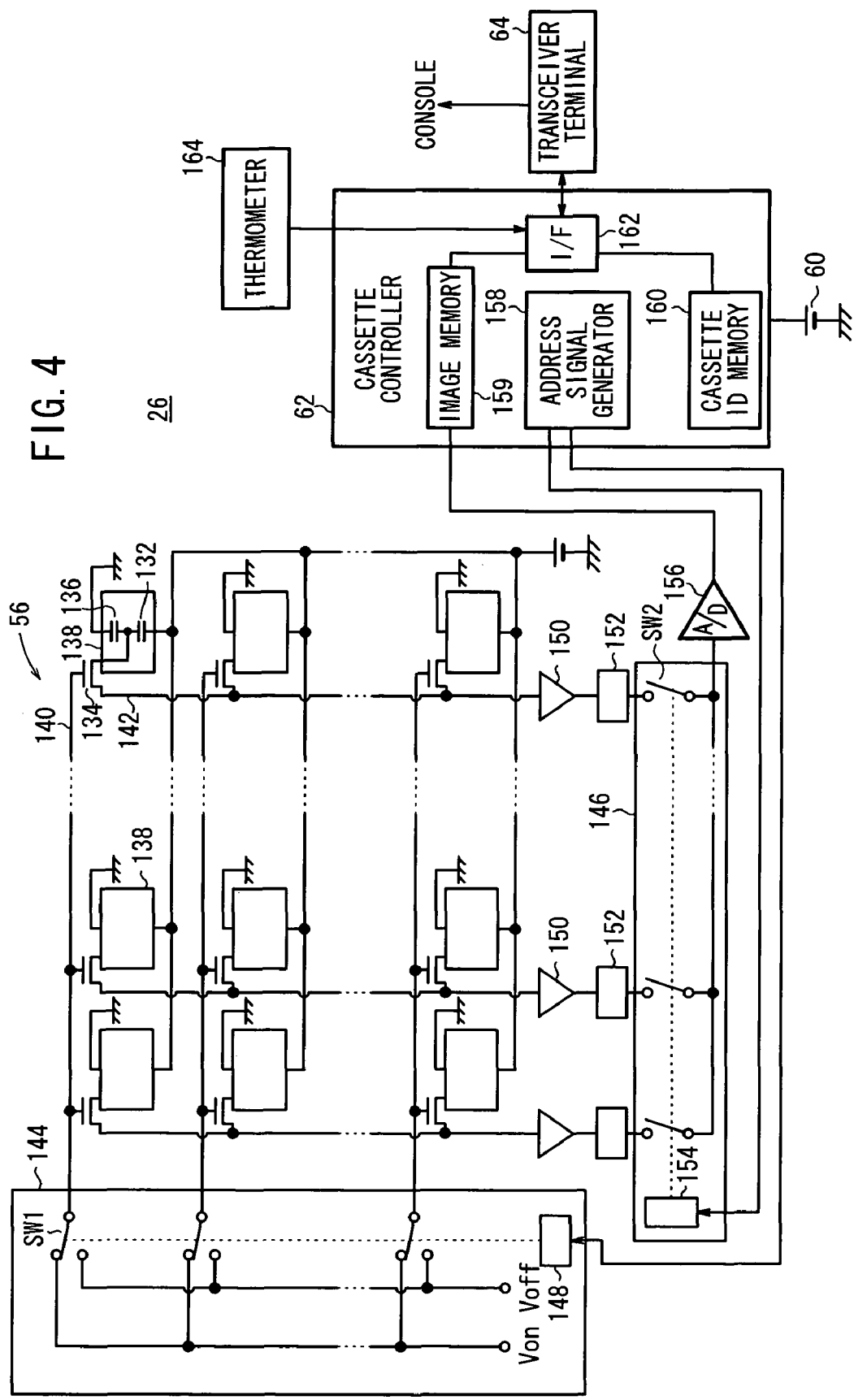
FIG. 4 is a block diagram of a radiation detector in the electronic cassette shown in FIG. 3 together with a cassette controller.

FIG. 4 shows in block form a circuit arrangement of the radiation detector 56 housed in the electronic cassette 26 and the cassette controller 62. As shown in FIG. 4, the radiation detector 56 comprises an array of thin-film transistors (TFTs) 134 arranged in rows and columns, a photoelectric conversion layer 132 made of a material such as amorphous selenium (a-Se) for generating electric charges upon detection of radiation X, the photoelectric conversion layer 132 being disposed on the array of TFTs 134, and an array of storage capacitors 136 connected to the photoelectric conversion layer 132. When radiation X is applied to the radiation detector 56, electric charges are generated in the photoelectric conversion layer 132, and the storage capacitors 136 store the generated electric charges. Then, the TFTs 134 are turned on one row at a time in order to read electric charges from the storage capacitors 136 as an image signal. In FIG. 4, the photoelectric conversion layer 132 and one of the storage capacitors 136 are shown as making up one pixel 138, and the pixel 138 is connected to one of the TFTs 134. Details of the other pixels 138, which are the same as those of the illustrated pixel 138, have been omitted from illustration. Since amorphous selenium tends to be changed in structure and lose functions thereof at high temperatures, amorphous selenium needs to be used within a certain temperature range. Therefore, some means for cooling the radiation detector 56 should preferably be provided in the electronic cassette 26.

The TFTs 134 connected to the respective pixels 138 are connected to respective gate lines 140 that extend in parallel to the rows, and to respective signal lines 142 that extend in parallel to the columns. The gate lines 140 are connected to a line scanning driver 144, and the signal lines 142 are connected to a multiplexer 146, which serves as a reading circuit.

The gate lines 140 are supplied with control signals Von, Voff from the line scanning driver 144 for turning on and off the TFTs 134 along the rows. The line scanning driver 144 comprises a plurality of switches SW1 for switching between the gate lines 140, and an address decoder 148 for outputting selection signals for selecting one of the switches SW1 at a time. The address decoder 148 is supplied with an address signal from the cassette controller 62.

The signal lines 142 are supplied with electric charges, which are stored in the storage capacitors 136 of the pixels 138, through the TFTs 134 arranged in the columns. Electric charges supplied to the signal lines 142 are amplified by amplifiers 150, which are connected respectively to the signal lines 142. The amplifiers 150 are connected through respective sample and hold circuits 152 to the multiplexer 146. The multiplexer 146 comprises a plurality of switches SW2 for successively switching between the signal lines 142, and an address decoder 154 for outputting selection signals for selecting one of the second switches SW2 at a time. The address decoder 154 is supplied with an address signal from the cassette controller 62. The multiplexer 146 has an output terminal connected to an A/D converter 156. A radiation image signal generated by the multiplexer 146 based on electric charges from the sample and hold circuits 152 is converted by the A/D converter 156 into digital image signals representing the radiation image information, and the digital image signals are supplied to the cassette controller 62.

The cassette controller 62 comprises an address signal generator 158 for supplying address signals to the address decoder 148 of the line scanning driver 144 and the address decoder 154 of the multiplexer 146 of the radiation detector 56, an image memory 159 for storing radiographic image information detected by the radiation detector 56, a cassette ID memory 160 for storing cassette ID information for identifying the electronic cassette 26, and an interface 162.

The interface 162 receives a request to send radiographic image information through the transceiver terminal 64, and sends the cassette ID information stored in the cassette ID memory 160, and the radiographic image information stored in the image memory 159 through the transceiver terminal 64.

The electronic cassette 26 has an offset value called a dark current, which is detected when the electronic cassette 26 is not irradiated with radiation X. The offset value is produced by a leakage current from each of the pixels. When instructed by the console 28, the cassette controller 62 for the electronic cassette 26 reads image information generated by the electronic cassette 26 when the electronic cassette 26 is not irradiated with radiation X, stores the read image information as offset image information in the image memory 159, and sends the offset image information from the image memory 159 through the transceiver terminal 64 to the console 28. The offset value varies over time and also varies with the temperature of the radiation detector 56. Therefore, the offset value of the electronic cassette 26 should preferably be read when the environmental temperature is substantially constant, and after the electric charges representative of radiographic image information in the previous image capturing cycle have sufficiently been discharged, e.g., at a time when the medical organization 12 begins business hours and the console 28 is initially activated. Since image information includes both radiographic image information and the offset image information, the term "image information" will hereinafter be used as a collective term, representing both radiographic image information and offset image information.

The electronic cassette 26 includes a thermometer 164 for detecting the environmental temperature around the electronic cassette 26. Temperature data from the thermometer 164 is sent to the console 28 via the interface 162 and the transceiver terminal 64.

Temperature data sent to the console 28 are stored together with a date and a measurement time in a history information file of usage status, which is registered in a memory (not shown) in the console 28. The history information file also stores information concerning the tube voltage of the radiation source, etc., in addition to the temperature data.

Figure 5:
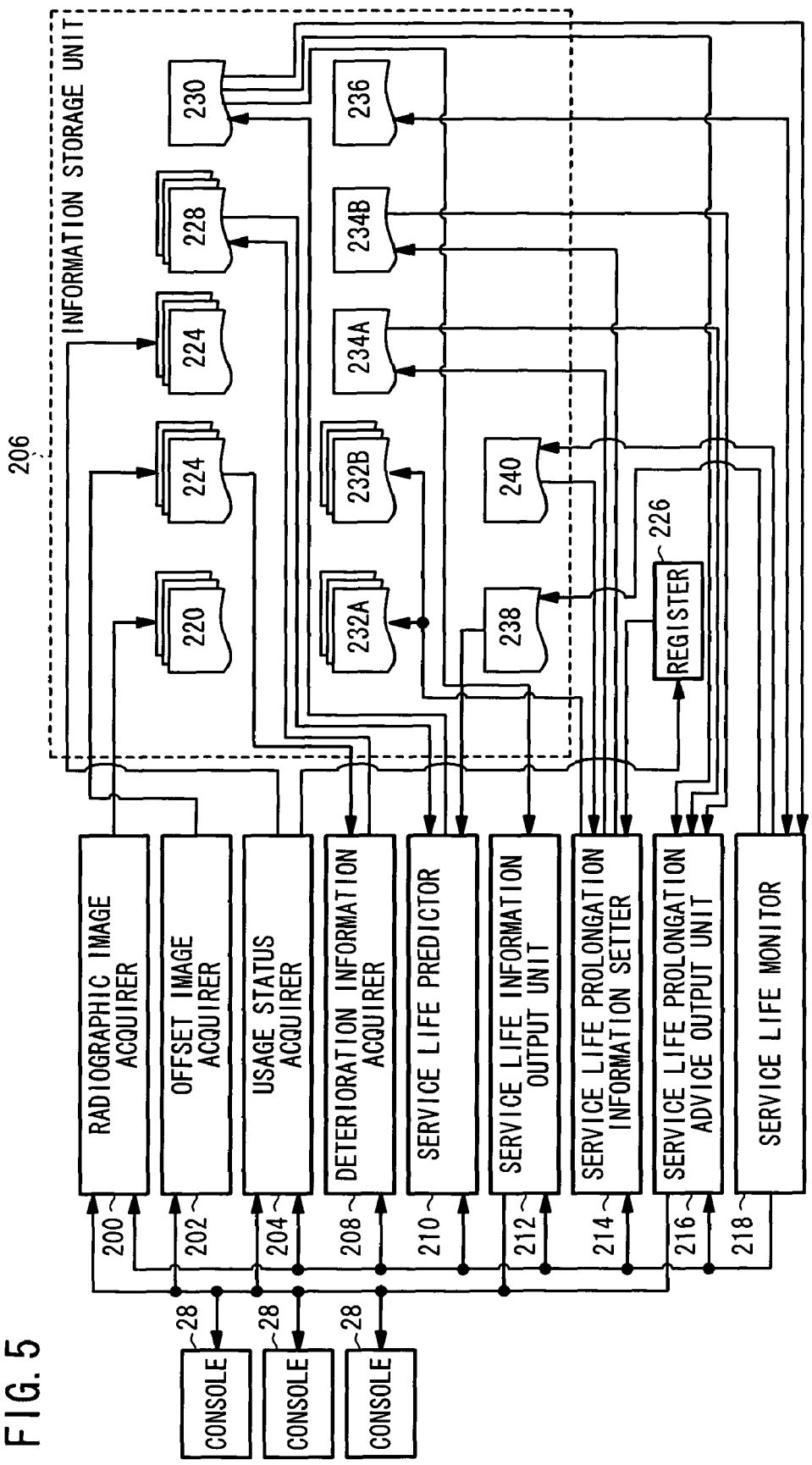
FIG. 5 is a block diagram showing various functional sections of the remote manager.

As shown in FIG. 5, the remote manager 20 comprises, as functional sections, a radiographic image acquirer 200, an offset image acquirer 202, a usage status acquirer 204, an information storage unit 206, a deterioration information acquirer 208, a service life predictor 210, a service life information output unit 212, a service life prolongation information setter 214, a service life prolongation advice output unit 216, and a service life monitor 218, which activates and controls the functional sections and determines electronic cassettes 26 the service lives of which are to be predicted. The remote manager 20 also outputs to the consoles 28 image capturing conditions, patient information, etc., produced by the doctor or a radiological technician.

The radiographic image acquirer 200 outputs radiographic image transfer request signals for requesting the respective consoles 28 to transfer radiographic image information 220 to the remote manager 20, receives the radiographic image information 220 from the consoles 28, and stores the received radiographic image information 220 in the information storage unit 206 in chronological order. Hereinafter, it shall be assumed that transfer request signals are output to the respective consoles 28 in order to request the respective consoles 28 to transfer various items of information to the remote manager 20.

The offset image acquirer 202 outputs offset image transfer request signals requesting the respective consoles 28 to transfer offset image information 222, receives the offset image information 222 from the consoles 28, and stores the received offset image information 222 in the information storage unit 206 in chronological order.

The usage status acquirer 204 outputs usage status transfer request signals requesting the respective consoles 28 to transfer usage status history information 224, receives the usage status history information 224 from the consoles 28, and stores the received usage status history information 224 in the information storage unit 206 in chronological order. The usage status acquirer 204 also reads latest temperature data and tube voltages of the respective electronic cassettes 26 from the status history information 224 stored in the information storage unit 206, and temporarily stores the latest (i.e., the most recent) temperature data and tube voltage in a register 226.

The deterioration information acquirer 208 acquires information concerning the extent of deterioration of the electronic cassettes 26 based on the latest offset image information 222, among at least one item of offset image information 222 stored in the information storage unit 206. More specifically, the deterioration information acquirer 208 detects an area that is not functioning properly as a pixel, i.e., a pixel defect (a spot defect or a linear defect), from the latest offset image information 222, and registers the address and size of the pixel defect in a defect information table 228. For example, if a pixel defect of one pixel is detected, the address of the pixel is registered as an address of an original defective pixel, and "1" is registered as the size of the pixel defect. If a pixel adjacent to the original defective pixel subsequently becomes defective over time, then each time that the deterioration information acquirer 208 performs a defect detecting process, the address of the original defective pixel is continuously registered, and the number of pixels adjacent to the original defective pixel, which are detected as additional pixel defects, is added together as a sum, and the sum is registered as the size of the pixel defects. Therefore, the growth over time of pixel defects, starting with the original defective pixel, can be recognized by referring to the defect information table 228, which stores the pixel defect information in chronological order.

A pixel defect (including an original defective pixel) is detected as follows: Among the offset image information 222, one item of image information corresponding to a central area of about 100 mm×100 mm, and four items of image information corresponding to four areas of about 100 mm×100 mm, which surround the central area, are calculated in order to determine RMS values thereof. Thereafter, among the offset image information 222, a pixel having a value that deviates from the calculated RMS value is defined as a defective pixel.

The information storage unit 206 includes a number of groups of defect information tables 228 arranged in chronological order, which is the same as the number of electronic cassettes 26. Defect information tables 228, which may be used for two or more years, are assigned to each of the electronic cassettes 26.

Figure 6:
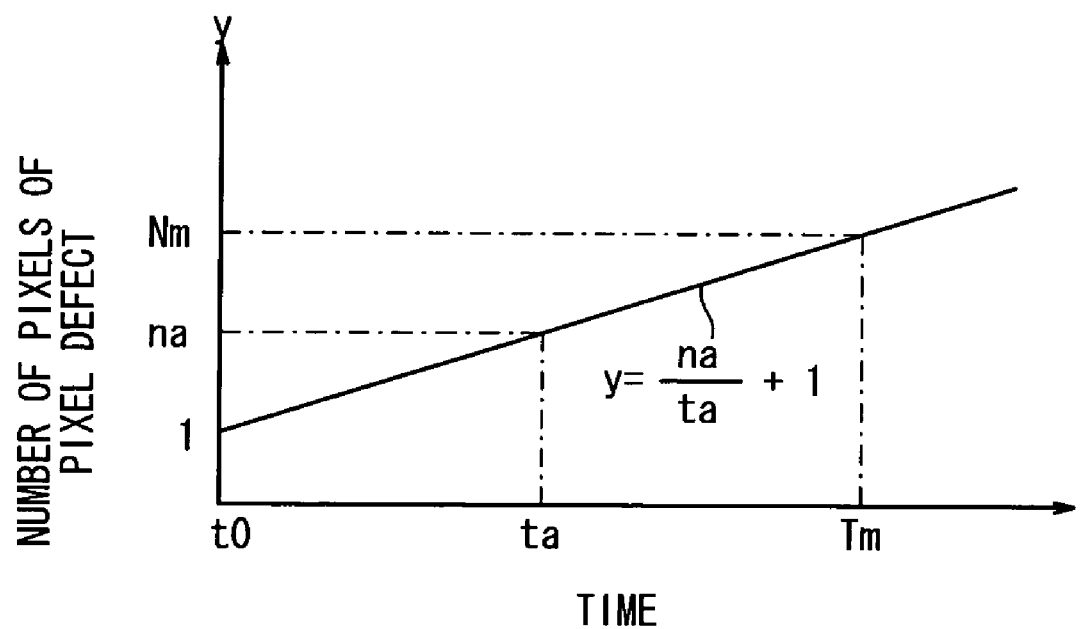
FIG. 6 is a diagram showing a graph representing a rate of growth of pixel defects and a process of predicting service life.
Figure 7:
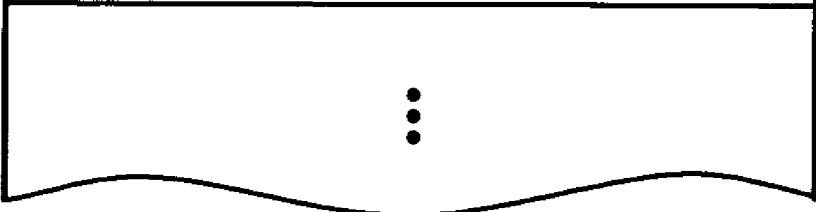
FIG. 7 is a diagram showing by way of example contents of a service life information table.

The service life predictor 210 predicts the service life, respectively, of the electronic cassettes 26 from the defect information tables 228 arranged in chronological order. A process performed by the service life predictor 210 for predicting the service life of one of the electronic cassettes 26 will be described below. The rate of growth of each of the pixel defects registered in a plurality of defect information tables 228, which are arranged in a chronological order that corresponds to the electronic cassette 26, is calculated. More specifically, when an original defective pixel is produced at a certain time, it is assumed that the size of the pixel defect is 1. A characteristic curve representing how the size of the pixel defect changes over time, e.g., a straight-line equation, is determined based on the size of the pixel defect corresponding to the address of the original defective pixel among the latest defect information table 228, and the time at which the size of the pixel defect according to the straight-line equation becomes a size (upper limit) of a pixel defect that requires the electronic cassette 26 to be replaced. For example, FIG. 6 shows a graph having a horizontal axis representing time and a vertical axis representing the number of pixels (including an original defective pixel) making up a pixel defect. It is assumed that when the electronic cassette 26 starts to be used, a defective pixel, i.e., an original defective pixel, is found at time t0. As time goes on, the number of defective pixels increases. It is assumed that the number of pixels that make up one pixel defect reaches na upon elapse of several months, i.e., at an elapsed time ta. In this case, the characteristic curve representing how the size of the pixel defect changes with time is approximated by a straight-line equation: y=(na/ta)+1 where y indicates the number of pixels of one pixel defect. The characteristic curve has a gradient na/ta. The time Tm at which the value of y reaches the upper limit value Nm is determined, and the elapsed time ta up to the present is subtracted from the time Tm in order to determine the time at which the size of the pixel defect based on the original defective pixel reaches the upper limit value Nm, i.e., to predict the service life. The above calculating process is carried out with respect to each of the original defective pixels of the electronic cassette 26, and the time at which the size of the pixel defect reaches the upper limit value Nm within a shortest period is registered in a service life information table 230 as the effective service life of the electronic cassette 26. The service life information table 230 registers therein, in addition to the service life of the respective electronic cassettes 26, characteristic curve gradients of the respective electronic cassettes 26, the latest environmental temperatures of the respective electronic cassettes 26, and the latest tube voltages for each of the respective electronic cassettes 26. As shown in FIG. 7, the service life information table 230 contains as many records as the number of electronic cassettes 26, each record registering therein the ID number (cassette number) of the corresponding electronic cassette 26, the ID number (console number) of the console 28 that governs the electronic cassette 26, the service life of the electronic cassette 26, the latest environmental temperature of the electronic cassette 26, and the latest tube voltage for the electronic cassette 26.

The service life information output unit 212 reads the registered contents from the service life information table 230, assembles the read contents into a message template to generate message information concerning service life (service life message information), and outputs the service life message information to the corresponding console 28.

The service life prolongation information setter 214 sets information concerning a new usage status required to prolong the predicted service life, based on the relationship between the usage status of a preset electronic cassette 26 and deterioration of the electronic cassette 26, as well as information concerning the acquired usage status. More specifically, it is known that the rate of growth of pixel defects in the radiation detector 56 of an electronic cassette 26 is governed by the environmental temperature of the electronic cassette 26 and the dose of radiation applied to the electronic cassette 26. As the environmental temperature of the electronic cassette 26 becomes lower, the rate of growth of pixel defects in the radiation detector 56 also becomes lower. As the dose of radiation applied to the electronic cassette 26 becomes smaller, i.e., as the tube voltage is lower, the rate of growth of pixel defects in the radiation detector 56 also becomes lower. Therefore, a plurality of samples of radiation detectors 56 provided in electronic cassettes 26 are prepared and experimented on, and rates of growth of pixel defects at a plurality of environmental temperatures (i.e., characteristic curves representing how the size of pixel defects changes with time; gradients of straight-line equations, for example, gradients of characteristic curves) are determined according to a process similar to the above-described process carried out by the deterioration information acquirer 208. The determined rates of growth are averaged in order to generate a first map 232A, i.e., a map concerning the rate of growth of pixel defects at different environmental temperatures. The rate of growth may be plotted at environmental temperatures separated by intervals of 5° C., for example. If it is desired that the rate of growth be recognized at smaller intervals, then the rate of growth may be plotted at environmental temperature intervals of 1° C. or 3° C. If it is desired that the rate of growth be recognized at greater intervals, then the rate of growth may be plotted at environmental temperature intervals of 7° C. or 10° C. In other words, the rate of growth may be plotted at any environmental temperature intervals desired by the user.

Similarly, rates of growth of pixel defects at a plurality of tube voltages are determined according to a process, which is similar to the aforementioned process, and which is carried out by the deterioration information acquirer 208. The determined rates of growth are averaged in order to generate a second map 232B, i.e., a map relating to the rate of growth of pixel defects at the tube voltages. The rate of growth may be plotted at tube voltages separated by intervals of 5 keV, for example. If it is desired that the rate of growth be recognized at smaller intervals, then the rate of growth may be plotted at tube voltage intervals of 1 keV or 3 keV. Alternatively, if it is desired that the rate of growth be recognized at greater intervals, then the rate of growth may be plotted at tube voltage intervals of 7 keV or 10 keV. In other words, the rate of growth may be plotted at any tube voltage intervals desired by the user.

The service life prolongation information setter 214 reads at least one characteristic curve (e.g., a straight-line equation) from the first map 232A having a gradient that is smaller than the characteristic curve gradients registered in the service life information table 230, recalculates a pixel defect determined to reach the upper limit value Nm within the shortest period based on the read characteristic curve (candidate characteristic curve), and registers in a first service life prolongation information table 234A the time at which the size of the pixel defect will reach the upper limit value Nm as the prolonged service life of the electronic cassette 26. The first service life prolongation information table 234A also registers therein, in addition to the prolonged service lives of the respective electronic cassettes 26, an environmental temperature on which the candidate characteristic curve is based, which is registered as an environmental temperature to be set. For example, if there are two candidate characteristic curves for an electronic cassette 26, two prolonged service lives for the electronic cassette 26 and corresponding environmental temperatures are registered in the first service life prolongation information table 234A. More specifically, as shown in FIG. 8A, the first service life prolongation information table 234A has the same number of records as the number of electronic cassettes 26, and each record registers therein the ID number (cassette number) of the corresponding electronic cassette 26, the ID number (console number) of the console 28 that governs the electronic cassette 26, and prolonged service lives and environmental temperatures corresponding to the two candidate characteristic curves.

Since, as described above, it is assumed in the present embodiment that the characteristic curve representing how the size of the pixel defect changes with time is approximated by a straight-line equation, at least one characteristic curve having a gradient that is smaller than the characteristic curve gradients registered in the service life information table 230 is read from the first map 232A as a candidate characteristic curve. However, a candidate characteristic curve may be selected according to other rules, to be described below. Such other rules are preferable if the characteristic curve representing how the size of the pixel defect changes over time is not represented by a straight-line equation, but by a linear equation. Specifically, since the rate of growth of pixel defects in the radiation detector 56 becomes lower as the environmental temperature of the electronic cassette 26 becomes lower, a characteristic curve at an environmental temperature lower than the latest temperature data (the temperature data temporarily stored in the register 226) is read from the first map 232A, and a pixel defect determined so as to reach the upper limit value Nm within the shortest period is recalculated. Then, the time at which the size of the pixel defect will reach the upper limit value Nm is registered in the first service life prolongation information table 234A as the prolonged service life of the electronic cassette 26. The first service life prolongation information table 234A registers therein, in addition to the prolonged service lives of the respective electronic cassettes 26, an environmental temperature to be set. The characteristic curve at an environmental temperature lower than the latest temperature data may be represented by only one characteristic curve at an environmental temperature, which is one stage lower than the latest temperature data. In such a case, one prolonged service life of each of the electronic cassettes 26 along with an environmental temperature to be set are registered in the first service life prolongation information table 234A. Alternatively, the characteristic curve at an environmental temperature lower than the latest temperature data may be represented by a plurality of characteristic curves at an environmental temperature, which is one stage through several stages lower than the latest temperature data. In such a case, a plurality of prolonged service lives of each of the electronic cassettes 26 along with environmental temperatures to be set are registered in the first service life prolongation information table 234A.

The service life prolongation information setter 214 reads from the second map 232B at least one characteristic curve (e.g., a straight-line equation) having a gradient that is smaller than the characteristic curve gradients registered in the service life information table 230, recalculates a pixel defect determined to reach the upper limit value Nm within the shortest period based on the read characteristic curve (candidate characteristic curve), and registers in a second service life prolongation information table 234B the time at which the size of the pixel defect will reach the upper limit value Nm as the prolonged service life of the electronic cassette 26. The second service life prolongation information table 234B registers therein, in addition to the prolonged service lives of the respective electronic cassettes 26, a tube voltage on which the candidate characteristic curve is based, which is registered as a tube voltage to be set. For example, if there are two candidate characteristic curves for an electronic cassette 26, two prolonged service lives for the electronic cassette 26 and corresponding tube voltages are registered in the second service life prolongation information table 234B. More specifically, as shown in FIG. 8B, the second service life prolongation information table 234B has the same number of records as the number of electronic cassettes 26, and each record registers therein the ID number (cassette number) of the corresponding electronic cassette 26, the ID number (console number) of the console 28 that governs the electronic cassette 26, and prolonged service lives and tube voltages corresponding to the two candidate characteristic curves.

Since, as described above, in the present embodiment it is assumed that the characteristic curve representing how the size of the pixel defect changes over time is approximated by a straight-line equation, at least one characteristic curve having a gradient that is smaller than the characteristic curve gradients registered in the service life information table 230 is read from the second map 232B as a candidate characteristic curve. However, a candidate characteristic curve may be selected according to other rules, to be described below. Such other rules are preferable if the characteristic curve representing how the size of the pixel defect changes with time is not represented by a straight-line equation, but by a linear equation. More specifically, since the rate of growth of pixel defects in the radiation detector 56 becomes lower as the tube voltage becomes lower, a characteristic curve at a tube voltage lower than the latest tube voltage data (i.e., the tube voltage data temporarily stored in the register 226) is read from the second map 232B, and a pixel defect determined to reach the upper limit value Nm within the shortest period is recalculated. Then, the time at which the size of the pixel defect will reach the upper limit value Nm is registered in the second service life prolongation information table 234B as the prolonged service life of the electronic cassette 26. The second service life prolongation information table 234B registers therein, in addition to the prolonged service lives of the respective electronic cassettes 26, tube voltages to be set. The characteristic curve at a tube voltage lower than the latest tube voltage data may be represented by only one characteristic curve at a tube voltage, which is one stage lower than the latest tube voltage data. In such a case, one prolonged service life of each of the electronic cassettes 26 along with tube voltages to be set are registered in the second service life prolongation information table 234B. Alternatively, the characteristic curve at a tube voltage lower than the latest tube voltage data may be represented by a plurality of characteristic curves at tube voltages, which are one stage through several stages lower than the latest tube voltage data. In such a case, a plurality of prolonged service lives of each of the electronic cassettes 26 along with tube voltages to be set are registered in the second service life prolongation information table 234B.

The service life prolongation advice output unit 216 reads the contents of the service life information table 230 and the first service life prolongation information table 234A, assembles the read contents into a message template to generate first service life prolongation message information concerning service life prolongation based on environmental temperature, and outputs the first service life prolongation message information to the corresponding console 28. The service life prolongation advice output unit 216 also reads the contents of the service life information table 230 and the second service life prolongation information table 234B, assembles the read contents into a message template to generate second service life prolongation message information concerning service life prolongation based on tube voltage, and outputs the second service life prolongation message information to the corresponding console 28.

The service life monitor 218 controls processing sequences to be performed periodically with respect to each of the electronic cassettes 26 for at least the offset image acquirer 202, the usage status acquirer 204, the deterioration information acquirer 208, the service life predictor 210, and the service life information output unit 212.

First, the service life monitor 218 uses an information table (cassette information table 236) stored in the information storage unit 206, which has the same number of records as the number of electronic cassettes 26. As shown in FIG. 9, each of the records of the cassette information table 236 registers therein the ID number (cassette number) of the corresponding electronic cassette 26, the ID number (console number) of the console 28 that governs the electronic cassette 26, and a date for predicting the service life. The service life monitor 218 controls processing sequences to be performed periodically at preset time intervals. When the service life monitor 218 is activated, dates based on the preset time intervals are registered in the records. If the present date agrees with one of the dates registered in the cassette information table 236, the cassette number and the console number of the electronic cassette 26 bearing that date are registered as an object to be predicted for service life in a list-format file (to-be-predicted cassette list 238), and the service life monitor 218 activates various functional sections, including the service life predictor 210, etc. The service life predictor 210, etc., which are activated by the service life monitor 218, perform the above process of predicting a service life with respect to electronic cassettes 26 registered in the to-be-predicted cassette list 238. In the cassette information table 236, records therein corresponding to the electronic cassettes 26 registered in the to-be-predicted cassette list 238 include a next date registered based on the preset time intervals. In this manner, the above processing sequences with respect to each of the electronic cassettes 26, i.e., processing sequences over the offset image acquirer 202, the usage status acquirer 204, the deterioration information acquirer 208, the service life predictor 210, the service life information output unit 212, the service life prolongation information setter 214, and the service life prolongation advice output unit 216, are performed individually and periodically.

The periodic processing sequence may be performed over the offset image acquirer 202, the usage status acquirer 204, the deterioration information acquirer 208, the service life predictor 210, and the service life information output unit 212. Further, the processing sequence may be performed over the service life prolongation information setter 214 and the service life prolongation advice output unit 216 at certain times. For example, the service life monitor 218 may perform the following processing sequence:

The service life monitor 218 monitors whether or not service lives of the respective electronic cassettes 26, which have been registered in the service life information table 230, have fallen within a preset threshold value (time). If the service life of a certain electronic cassette 26 has fallen within the preset threshold value, then the service life monitor 218 registers the ID number (cassette number) of the electronic cassette 26, i.e., an electronic cassette 26 the service life of which is approaching an end, in a list-format file (service life prolongation file 240), and activates the service life prolongation information setter 214 and the service life prolongation advice output unit 216. For the electronic cassette 26 the service life of which is approaching an end, the time intervals (periodic time intervals) of the periodic processing sequence over the offset image acquirer 202, the usage status acquirer 204, the deterioration information acquirer 208, and the service life predictor 210 are shortened by about one-half the normal time intervals, for example, thereby allowing the doctor or radiological technician to reliably have an opportunity to take actions to prolong the service life of the electronic cassette 26.

Rather than the above processing sequence, the service life monitor 218 may perform the following processing sequence: The service life monitor 218 may periodically perform the above processing sequence over the offset image acquirer 202, the usage status acquirer 204, the deterioration information acquirer 208, and the service life predictor 210. When the service life monitor 218 has performed the processing sequence one or a plurality of times, the service life monitor 218 registers the ID numbers of all of the electronic cassettes 26 in the service life prolongation file 240, and then in repetitive cycles activates the service life prolongation information setter 214 and the service life prolongation advice output unit 216. Furthermore, depending on the extent of deterioration of each of the electronic cassettes 26, the service life monitor 218 may change the time intervals (periodic time intervals) of the periodic processing sequence over the offset image acquirer 202, the usage status acquirer 204, the deterioration information acquirer 208, and the service life predictor 210. Specifically, as each of the electronic cassettes 26 becomes deteriorated to a greater extent, the periodic time intervals may be made shorter, thereby enabling the doctor or radiological technician to reliably have an opportunity to take actions to prolong the service life of the electronic cassette 26.

Figure 10:
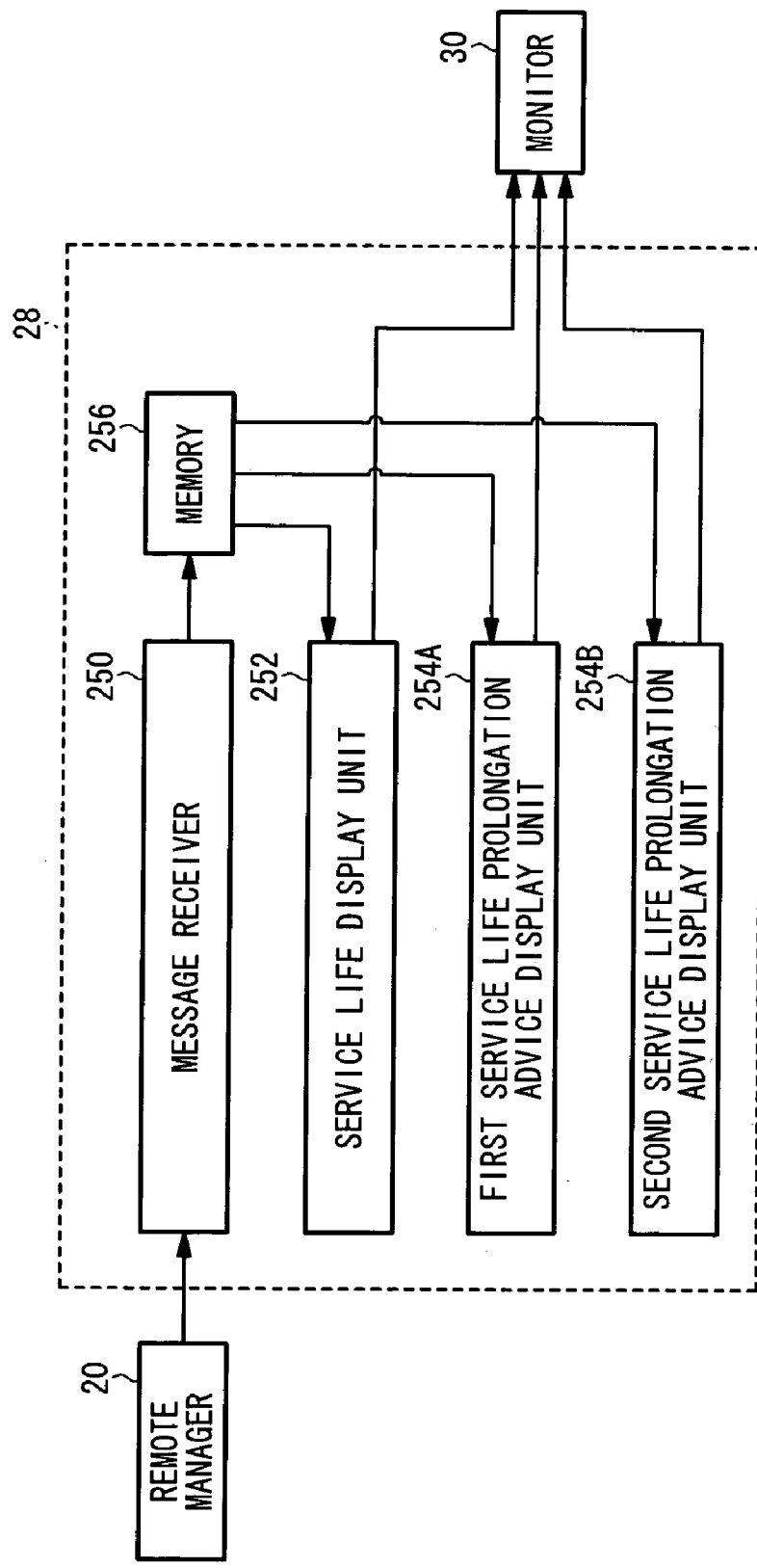
FIG. 10 is a block diagram showing various functional sections of each of the consoles.

As shown in FIG. 10, each of the consoles 28 comprises a message receiver 250, a service life display unit 252, a first service life prolongation advice display unit 254A, and a second service life prolongation advice display unit 254B.

The message receiver 250 receives service life message information, first service life prolongation information, and second service life prolongation information sent from the remote manager 20, and stores the information in a memory 256 in the console 28.

The display monitor 30 that is connected to the console 28 displays an icon for indicating the service life of an electronic cassette and two icons (environmental temperature and tube voltage) for indicating service life prolongation advice. When the doctor or radiological technician selectively clicks on such icons, the service life display unit 252, the first service life prolongation advice display unit 254A, and the second service life prolongation advice display unit 254B are selectively activated.

More specifically, when the doctor or radiological technician clicks on the icon indicating service life, the service life display unit 252 displays, on the display monitor 30, a service life display image 258 (see FIG. 11) for the electronic cassette 26 based on the service life message information stored in the memory 256. As shown in FIG. 11, the service life display image 258 displays items including the ID number (cassette number) of the electronic cassette 26 displayed in a first display area 260a, the service life displayed in a second display area 260b based on the present usage status of the electronic cassette 26, the environmental temperature displayed in a third display area 260c, and the tube voltage displayed in a fourth display area 260d, etc. Even when the display monitor 30 has been displaying an image capturing menu including image capturing conditions, patient information, etc., by selectively clicking on the icon indicating service life, the service life display image 258 can be displayed as a pop-up or inline image. Therefore, the doctor or radiological technician can confirm the service life of the electronic cassette 26 at any time.

Figure 12A:
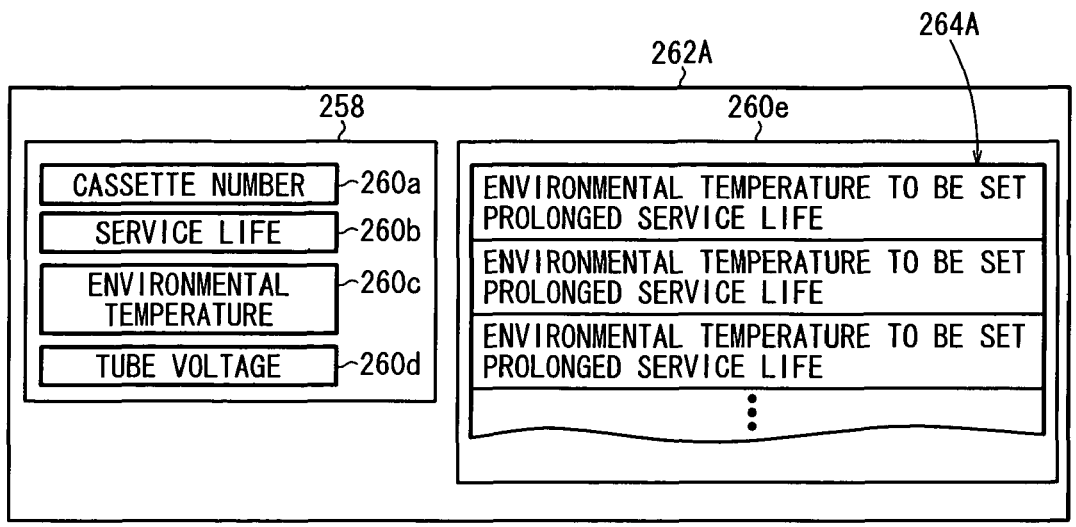
FIG. 12A is a diagram showing displayed items on a first service life prolongation advice display image.

The first service life prolongation advice display unit 254A is activated when the doctor or radiological technician selectively clicks on the icon indicating environmental temperature, and displays a first service life prolongation advice display image 262A (see FIG. 12A) in accordance with the environmental temperature for the electronic cassette 26, based on the first service life prolongation message information stored in the memory 256. As shown in FIG. 12A, the first service life prolongation advice display image 262A displays items including those in the service life display image 258, together with a first service life prolongation advice 264A displayed in a fifth display area 260e on the right side of the service life display image 258. The first service life prolongation advice 264A includes the same number of environmental temperatures to be set and prolonged service lives as the number of candidate characteristic curves, for example.

Figure 12B:
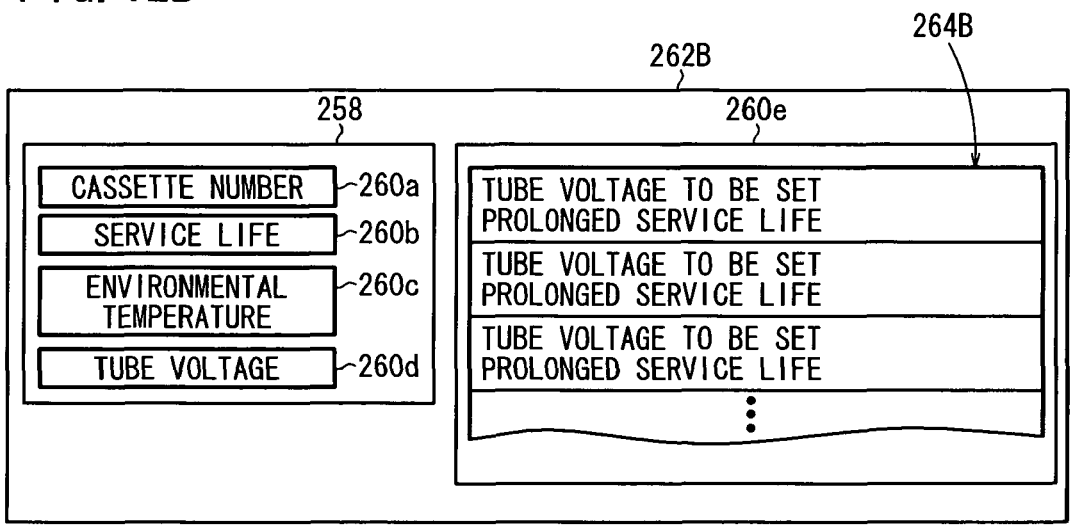
FIG. 12B is a diagram showing displayed items on a second service life prolongation advice display image.

The second service life prolongation advice display unit 254B is activated when the doctor or radiological technician selectively clicks on the icon indicating tube voltage, and displays a second service life prolongation advice display image 262B (see FIG. 12B) in accordance with the tube voltage for the electronic cassette 26, based on the second service life prolongation message information stored in the memory 256. As shown in FIG. 12B, the second service life prolongation advice display image 262B displays items including those in the service life display image 258, together with a second service life prolongation advice 264B displayed in a sixth display area 260f on the right side of the service life display image 258. The second service life prolongation advice 264B includes the same number of tube voltages to be set and prolonged service lives as the number of candidate characteristic curves, for example.

Even when the display monitor 30 is displaying an image capturing menu including image capturing conditions, patient information, etc., either of the first service life prolongation advice display unit 254A or the second service life prolongation advice display unit 254B can be displayed as a pop-up or inline image by selectively clicking on the icon for indicating environmental temperature or the icon indicating tube voltage. Therefore, the doctor or radiological technician can read and confirm the advice for service life prolongation at any time.

If the doctor or radiological technician wants to prolong the service life of the electronic cassette 26, then the doctor or radiological technician adjusts the temperature in the radiographic image capturing chamber 22 and a cooling function is performed on the electronic cassette 26 in order to change the present environmental temperature to the set environmental temperature, based on the first service life prolongation advice 264A displayed in the first service life prolongation advice display image 262A. Alternatively, the doctor or radiological technician changes the tube voltage which has been set in the console 28 in order to change the present tube voltage of the radiation source to the set tube voltage, based on the second service life prolongation advice 264B displayed in the second service life prolongation advice display image 262B. If the doctor or radiological technician judges that the service life of the electronic cassette 26 does not need to be prolonged, then the doctor or radiological technician does not adjust the environmental temperature based on the first service life prolongation advice display image 262A, and does not change the tube voltage based on the second service life prolongation advice display image 262B.

Figure 13:
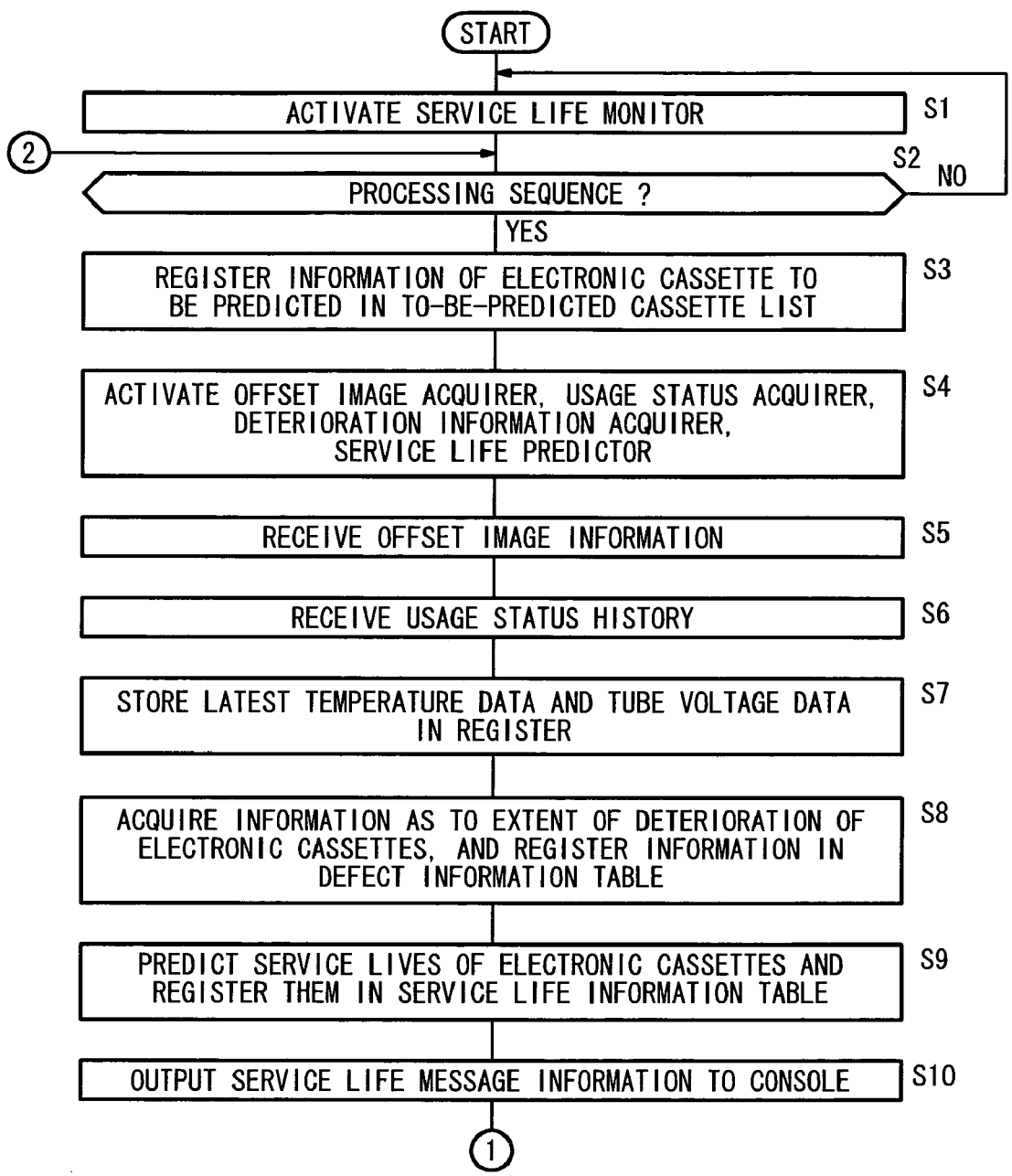
FIGS. 13 and 14 are flowcharts of a processing sequence of an offset image acquirer, a usage status acquirer, a deterioration information acquirer, a service life predictor, a service life information output unit, a service life prolongation information setter, a service life prolongation advice output unit, and a service life monitor.

Operations of the radiographic image capture managing system 10 according to the present embodiment will be described below with reference to FIGS. 13 through 15. Operations of the radiographic image capture managing system 10 primarily are carried out by the service life prolongation information setter 214 and the service life prolongation advice output unit 216, on electronic cassettes 26 the predicted service lives of which have fallen within the threshold value.

First, the processing sequence of the remote manager 20 will be described below. In step S1 shown in FIG. 13, when the remote manager 20 is activated, or when an input action is made on the remote manager 20 while the remote manager 20 is in operation, the service life monitor 218 is activated.

In step S2, the service life monitor 218 determines whether or not the processing sequence is to be performed over the offset image acquirer 202, the usage status acquirer 204, the deterioration information acquirer 208, and the service life predictor 210, based on timer information and calendar information in the remote manager 20. More specifically, the service life monitor 218 determines whether or not the processing sequence is to be performed by comparing with the present date the dates that are registered in the records of the cassette information table 236. If none of the dates registered in the records of the cassette information table 236 is the same as the present date, then the service life monitor 218 finishes the operation and waits until the service life monitor 218 is activated again at a subsequent time.

If one of the dates registered in the records of the cassette information table 236 is the same as the present date, then control proceeds to step S3, in which information (the cassette number and the console number) of the electronic cassette 26, which is registered in the record with the same date, is registered in the to-be-predicted cassette list 238.

Subsequently, in step S4, the service life monitor 218 activates the processing sequence over the offset image acquirer 202, the usage status acquirer 204, the deterioration information acquirer 208, and the service life predictor 210. If a process for shortening the periodic time intervals for a certain electronic cassette 26 is not present, then the information concerning all of the electronic cassettes 26 normally is registered in the to-be-predicted cassette list 238, and hence the processing sequence is carried out on all of the electronic cassettes 26.

In step S5 and thereafter, the offset image acquirer 202, the usage status acquirer 204, the deterioration information acquirer 208, and the service life predictor 210 perform respective processes of their own.

In step S5, the offset image acquirer 202 outputs an offset image transfer request signal for requesting the consoles 28 governing the electronic cassettes 26, which are registered in the to-be-predicted cassette list 238, to transfer the offset image information 222, receives the offset image information 222 transferred from the consoles 28, and stores the received offset image information 222 in the information storage unit 206 in chronological order.

In step S6, the usage status acquirer 204 outputs a usage status transfer request signal for requesting the consoles 28 governing the electronic cassettes 26, which are registered in the to-be-predicted cassette list 238, to transfer the usage status history information 224, receives the usage status history information 224 transferred from the consoles 28, and stores the received usage status history information 224 in the information storage unit 206 in chronological order.

In step S7, the usage status acquirer 204 reads, from among the usage status history information 224 stored in the information storage unit 206, the latest temperature data and tube voltage data concerning the electronic cassettes 26, and temporarily stores the read latest temperature data and tube voltage data in the register 226.

In step S8, the deterioration information acquirer 208 acquires information concerning the extent of deterioration of the electronic cassettes 26 based on the latest offset image information 222, for example, among at least one item of offset image information 222 stored in the information storage unit 206. As described in detail above, the deterioration information acquirer 208 detects an area not functioning properly as a pixel, i.e., a pixel defect (a spot defect or a linear defect), from the latest offset image information 222, and registers the address and size of the pixel defect in the defect information table 228.

In step S9, the service life predictor 210 predicts the service lives of the electronic cassettes 26 from the defect information tables 228 arranged in chronological order. As described in detail above, the service life predictor 210 registers, as service lives of the electronic cassettes 26 in the service life information table 230, times at which the size of the pixel defect reaches the upper limit value within a shortest period. The service life information table 230 also registers therein, in addition to the service lives of the respective electronic cassettes 26, characteristic curve gradients of the respective electronic cassettes 26, the latest environmental temperatures of the respective electronic cassettes 26, and the latest tube voltages for the respective electronic cassettes 26.

In step S10, the service life information output unit 212 reads the registered contents from the service life information table 230, assembles the read contents into a message template to generate message information concerning service life (service life message information), and outputs the service life message information to the corresponding console 28.

Figure 14:
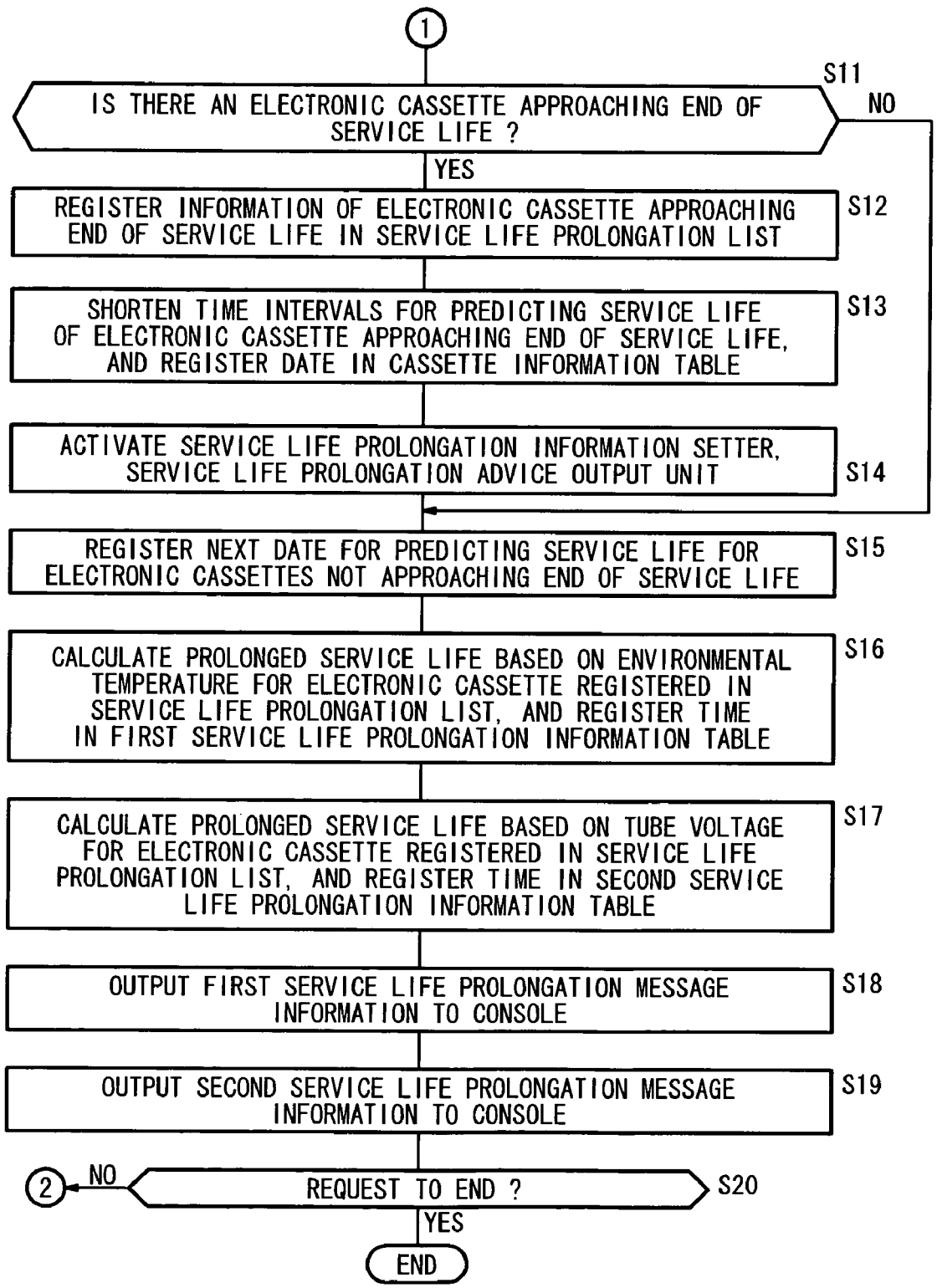

Thereafter, in step S11 shown in FIG. 14, the service life monitor 218 determines whether or not the electronic cassettes 26 registered in the service life information table 230 include an electronic cassette 26 (an electronic cassette 26 whose service life is approaching the completion thereof), the service life of which has fallen within a preset threshold value (time). Electronic cassettes 26 having service lives that are longer than the preset threshold value (time) are regarded as usable electronic cassettes 26, the service lives of which are not approaching completion thereof.

If the service life monitor 218 judges that the electronic cassettes 26 registered in the service life information table 230 include an electronic cassette 26 the service life of which is approaching the end thereof, then control proceeds to step S12, in which the service life monitor 218 registers the ID number (cassette number) of the electronic cassette 26 the service life of which is nearing its end in the service life prolongation file 240.

Thereafter, in step S13, the service life monitor 218 shortens the periodic time intervals and registers a date (a next date for predicting service life) in the cassette information table 236, based on the shortened periodic time intervals in the record corresponding to the electronic cassette 26 the service life of which is approaching the end thereof.

In step S14, the service life monitor 218 activates the service life prolongation information setter 214 and the service life prolongation advice output unit 216.

After the processing of step S14, or if in step S11 the service life monitor 218 judges that the electronic cassettes 26 registered in the service life information table 230 do not include an electronic cassette 26 the service life of which is approaching the end thereof, then in step S15, the service life monitor 218 registers a date (a next date for predicting service life) in the cassette information table 236, based on the preset periodic time intervals in the records corresponding to the electronic cassettes 26 whose service lives are still effective.

In step S16, the service life prolongation information setter 214, which was activated in step S14, reads from the first map 232A at least one characteristic curve (e.g., a straight-line equation) having a gradient that is smaller than the characteristic curve gradients registered in the service life information table 230, recalculates a pixel defect determined to reach the upper limit value within the shortest period based on the read characteristic curve (candidate characteristic curve), registers in the first service life prolongation information table 234A a time at which the size of the pixel defect will reach the upper limit value as the prolonged service life of the electronic cassette 26, and also registers the environmental temperature on which the candidate characteristic curve is based as an environmental temperature to be set in the first service life prolongation information table 234A. Alternatively, the service life prolongation information setter 214 reads from the first map 232A a characteristic curve at an environmental temperature lower than the latest temperature data (the temperature data temporarily stored in the register 226), recalculates a pixel defect determined to reach the upper limit value within the shortest period, registers in the first service life prolongation information table 234A a time at which the size of the pixel defect will reach the upper limit value as the prolonged service life of the electronic cassette 26, and also registers an environmental temperature to be set in the first service life prolongation information table 234A.

In step S17, the service life prolongation information setter 214 reads from the second map 232B at least one characteristic curve (e.g., a straight-line equation) having a gradient that is smaller than the characteristic curve gradients registered in the service life information table 230, recalculates a pixel defect determined to reach the upper limit value within the shortest period based on the read characteristic curve (candidate characteristic curve), registers in the second service life prolongation information table 234B a time at which the size of the pixel defect will reach the upper limit value as the prolonged service life of the electronic cassette 26, and also registers the tube voltage on which the candidate characteristic curve is based as a tube voltage to be set in the second service life prolongation information table 234B. Alternatively, the service life prolongation information setter 214 reads from the second map 232B a characteristic curve at a tube voltage lower than the latest tube voltage data (the tube voltage data temporarily stored in the register 226), recalculates a pixel defect determined to reach the upper limit value within the shortest period, registers in the second service life prolongation information table 234B a time at which the size of the pixel defect will reach the upper limit value as the prolonged service life of the electronic cassette 26, and also registers a tube voltage to be set in the second service life prolongation information table 234B.

In step S18, the service life prolongation advice output unit 216 reads the contents of the service life information table 230 and the first service life prolongation information table 234A, assembles the read contents into a message template so as to generate first service life prolongation message information concerning service life prolongation based on the environmental temperature, and outputs the first service life prolongation message information to the corresponding console 28.

In step S19, the service life prolongation advice output unit 216 reads the contents of the service life information table 230 and the second service life prolongation information table 234B, assembles the read contents into a message template so as to generate second service life prolongation message information concerning service life prolongation based on the tube voltage, and outputs the second service life prolongation message information to the corresponding console 28.

In step S20, the service life monitor 218 determines whether or not there is a request (a power cutoff request, a maintenance request, or the like) to terminate the service life monitoring process. If there is no such request to end the service life monitoring process, then the processing from step S2 is repeated. If there is a request to end the service life monitoring process, then the service life monitor 218 terminates the service life monitoring process.

The processing sequence for the console 28 will be described below with reference to the flowchart shown in FIG. 15.

Figure 15:
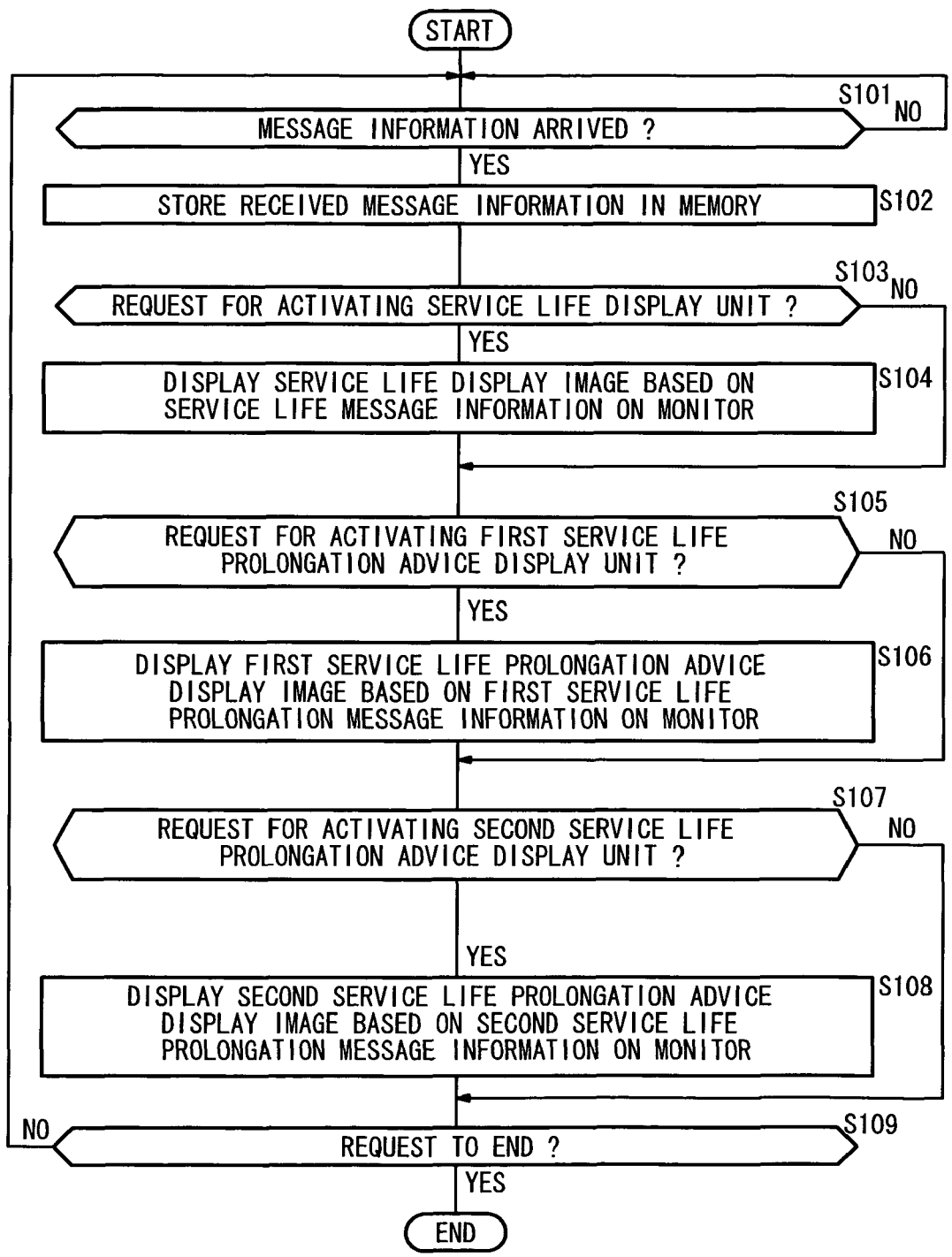
FIG. 15 is a flowchart of a processing sequence of a message receiver, a service life display unit, a first service life prolongation advice display unit, and a second service life prolongation advice display unit.

As shown in FIG. 15, in step S101, the message receiver 250 determines whether or not message information has arrived from the remote manager 20. If message information has arrived from the remote manager 20, then control proceeds to step S102, in which the message receiver 250 receives the message information and stores the message information according to type in the memory 256.

In step S103, the console 28 determines whether or not there is a request for activating the service life display unit 252, by determining whether the icon displayed on the display monitor 30 for indicating the service life has been selectively clicked.

If there is a request to activate the service life display unit 252, then in step S104, the console 28 activates the service life display unit 252 and performs the processing sequence for the service life display unit 252. More specifically, the service life display unit 252 generates the service life display image 258 (see FIG. 11) for the electronic cassette 26 based on the service life message information stored in the memory 256, and displays the service life display image 258 on the display monitor 30.

In step S105, the console 28 determines whether or not there is a request to activate the first service life prolongation advice display unit 254A, by determining whether the icon displayed on the display monitor 30 for indicating the service life prolongation advice (environmental temperature) has been selectively clicked.

If there is a request to activate the first service life prolongation advice display unit 254A, then in step S106, the console 28 activates the first service life prolongation advice display unit 254A and performs the processing sequence for the first service life prolongation advice display unit 254A. More specifically, the first service life prolongation advice display unit 254A generates the first service life prolongation advice display image 262A (see FIG. 12A) for the electronic cassette 26 based on the first service life prolongation message information stored in the memory 256, and displays the first service life prolongation advice display image 262A on the display monitor 30.

Then, in step S107, the console 28 determines whether there is a request to activate the second service life prolongation advice display unit 254B by determining whether or not the icon on the display monitor 30 for indicating the service life prolongation advice (tube voltage) has been selectively clicked.

If there is a request for activating the second service life prolongation advice display unit 254B, then in step S108, the console 28 activates the second service life prolongation advice display unit 254B and performs the processing sequence for the second service life prolongation advice display unit 254B. More specifically, the second service life prolongation advice display unit 254B generates the second service life prolongation advice display image 262B (see FIG. 12B) for the electronic cassette 26 based on the second service life prolongation message information stored in the memory 256, and displays the second service life prolongation advice display image 262B on the display monitor 30.

In step S109, the console 28 determines whether or not there is a request (a power cutoff request, a maintenance request, or the like) to terminate the service life display process and the service life prolongation advice display process. If there is no such request to end the service life display process and the service life prolongation advice display process, then processing from step S101 is repeated. If there is a request to end the service life display process and the service life prolongation advice display process, then the console 28 terminates the service life display process and the service life prolongation advice display process.

The operations described above according to the flowcharts shown in FIGS. 13 through 15 are performed primarily by the service life prolongation information setter 214 and the service life prolongation advice output unit 216 on electronic cassettes 26 the predicted service lives of which have fallen within the threshold value. However, as described above, these operations may be performed by the service life prolongation information setter 214 and the service life prolongation advice output unit 216 on all of the electronic cassettes 26, regardless of the threshold value. In such a case, the service life prolongation file 240 may be dispensed with, and the processes of steps S11 and S12 shown in FIG. 14 may also be dispensed with. The processing sequence over the offset image acquirer 202, the usage status acquirer 204, the deterioration information acquirer 208, and the service life predictor 210 may periodically be performed on all of the electronic cassettes 26, and after the processing sequence is performed a plurality of times, only the service life prolongation information setter 214 and the service life prolongation advice output unit 216 may be operated with respect to all of the electronic cassettes 26. In such a case, only the process of step S12 is changed. For example, after the processing sequence has been performed a plurality of times, the information of all of the electronic cassettes 26 may be registered in the service life prolongation file 240. The time intervals (periodic time intervals) of the periodic processing sequence over the offset image acquirer 202, the usage status acquirer 204, the deterioration information acquirer 208, and the service life predictor 210 may be changed depending on the extent of deterioration of each of the electronic cassettes 26. In this case, in step S13, the periodic time intervals may be made shorter as the extent of deterioration of each of the electronic cassettes 26 becomes greater.

Since the radiographic image capture managing system 10 according to the present embodiment is capable of predicting and indicating the service life of an electronic cassette 26 and also indicating an advice for prolonging the service life of an electronic cassette 26, the doctor or the radiological technician can take a positive action to prolong the service life of the electronic cassette 26 for thereby increasing the efficiency with which to use the electronic cassette 26. Since the increased efficiency with which to use the electronic cassette 26 contributes to a reduction in the running cost at the medical organizations 12, the practice of capturing radiographic images using the electronic cassette 26 will find widespread usage.

In the above embodiment, the service life of an electronic cassette 26 is predicted based on offset image information 222. However, the service life of an electronic cassette 26 may be predicted based on the radiographic image information 220. For example, each time a radiographic image is captured, brightness information of the radiographic image information 220 may be inspected, and any pixel the brightness information of which remains essentially unchanged over a plurality of cycles of capturing radiographic images may be judged as a defective pixel, after which the service life predicting process may be carried out as described above.

In the above embodiment, the service life of an electronic cassette 26 is predicted directly from defective pixels. However, the service life of an electronic cassette 26 may be predicted from a QL (Quantum Level) value, for example, of a phantom image representative of a QC phantom that generally is performed when a given radiographic image capturing practice is carried out.

In the radiographic image capture managing system 10 according to the illustrated embodiment, the radiation detector 56 housed in the electronic cassette 26 directly converts the dose of applied radiation X into electric signals with the photoelectric conversion layer 132 (direct conversion type). However, the radiographic image capture managing system 10 may employ a radiation detector (indirect conversion type radiation detector) including a scintillator for converting applied radiation X into visible light, and a solid-state detecting device made of amorphous silicon (a-Si) or the like for converting the visible light into electric signals (see Japanese Patent No. 3494683).

Alternatively, the radiographic image capture managing system 10 may employ a light readout type radiation detector for acquiring radiographic image information 220. Such a light readout type radiation detector operates as follows: When radiation is applied to a matrix of solid-state detecting devices, the solid-state detecting devices store an electrostatic latent image depending on the dose of applied radiation. For reading the stored electrostatic latent image, reading light is applied to the solid-state detecting devices in order to cause the solid-state detecting devices to generate an electric current representing the radiographic image information. When erasing light is applied to the radiation detector, the radiographic image information representing a residual electrostatic latent image is erased from the radiation detector, which can thus be reused (see Japanese Laid-Open Patent Publication No. 2000-105297).

If a light readout type radiation detector is used, a phantom image of a QC phantom may be used instead of the offset image information 222. In this case, the service life of an electronic cassette can be predicted from a QC (Quantum Level) value, whereupon service life prolongation advice can be generated.

In the above embodiment, the remote manager 20 for each of the medical organizations 12 includes the radiographic image acquirer 200, the offset image acquirer 202, the usage status acquirer 204, the information storage unit 206, the deterioration information acquirer 208, the service life predictor 210, the service life information output unit 212, the service life prolongation information setter 214, the service life prolongation advice output unit 216, and the service life monitor 218. Based thereon, the remote manager 20 predicts service lives of the electronic cassettes 26 and generates service life prolongation advice for each of the medical organizations 12. However, the central managing institution 14, which is separate from each of the medical organizations 12, may predict service lives of the electronic cassettes 26 and generate service life prolongation advice for the remote manager 20 of each of the medical organizations 12. In such a case, the central managing institution 14 may include the radiographic image acquirer 200, the offset image acquirer 202, the usage status acquirer 204, the information storage unit 206, the deterioration information acquirer 208, the service life predictor 210, the service life information output unit 212, the service life prolongation information setter 214, the service life prolongation advice output unit 216, and the service life monitor 218. Additionally, various tables and lists including the service life information table 230, the first service life prolongation information table 234A, and the second service life prolongation information table 234B may be provided for each of the medical organizations 12, to enable the various processing sequences described above to be performed. Alternatively, selected ones of the radiographic image acquirer 200, the offset image acquirer 202, the usage status acquirer 204, the information storage unit 206, the deterioration information acquirer 208, the service life predictor 210, the service life information output unit 212, the service life prolongation information setter 214, the service life prolongation advice output unit 216, and the service life monitor 218 may be installed in the central managing institution 14, whereas the others may be installed in the remote manager 20 of each of the medical organizations 12, so that the central managing institution 14 can predict service lives of electronic cassettes 26 and generate service life prolongation advice for the remote manager 20 of each of the medical organizations 12.

Figure 16:
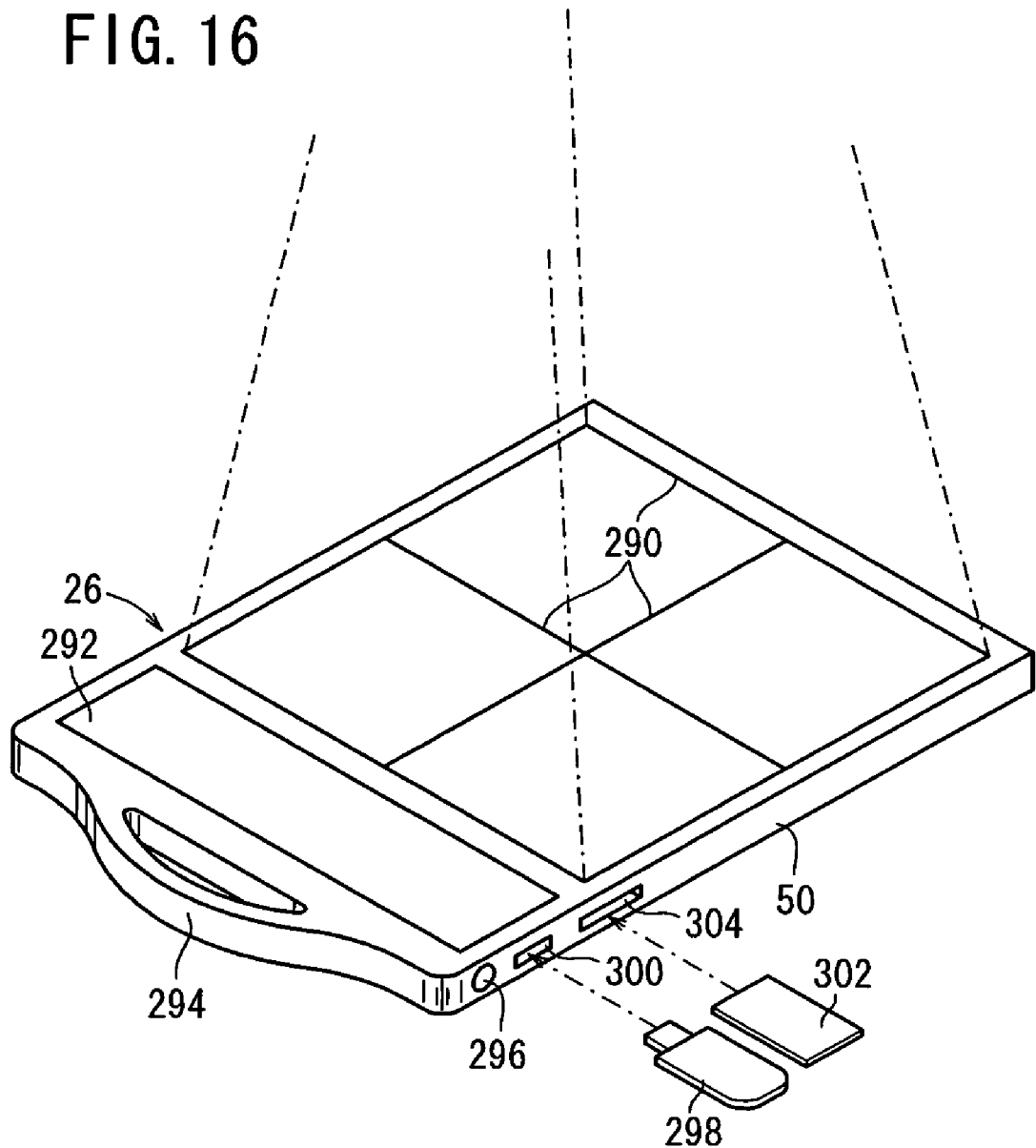
FIG. 16 is a perspective view of a modified electronic cassette.

FIG. 16 shows in perspective a modified electronic cassette 26.

As shown in FIG. 16, the modified electronic cassette 26 includes guide lines 290, which are drawn on the irradiated surface of a casing 50 to serve as a reference mark for an image capturing area and an image capturing position. Using such guide lines 290, the subject to be imaged, such as the patient, can be positioned with respect to the electronic cassette 26, and the range at which radiation X is applied to the electronic cassette 26 can be determined. Thus, radiographic image information can be recorded in an appropriate image capturing area of the electronic cassette 26.

The electronic cassette 26 also has a display unit 292 positioned outside of the image capturing area thereof for displaying various items of information concerning the electronic cassette 26. More specifically, the display unit 292 displays ID information of the subject whose radiographic image is recorded in the electronic cassette 26, the number of times that the electronic cassette 26 has been used, an accumulated exposure dose, the charged state (remaining power level) of the battery 60 housed in the electronic cassette 26, image capturing conditions associated with the radiographic image information, and a positioning image representing the subject positioned with respect to the electronic cassette 26, etc. The radiological technician can confirm the subject based on the ID information displayed on the display unit 292, and can also confirm in advance that the electronic cassette 26 is in a usable state. Then, the radiological technician can position the desired area to be imaged of the subject with respect to the electronic cassette 26 based on the displayed positioning image, whereby optimum radiographic image information can be captured using the electronic cassette 26.

The electronic cassette 26 includes a handle 294, which is gripped by the user to handle and carry the electronic cassette 26 with ease.

The electronic cassette 26 also has an input terminal 296 for connection to an AC adapter, a USB (Universal Serial Bus) terminal 300 for enabling insertion of a USB memory 298 therein, and a card slot 304 capable of receiving a memory card 302, all of which are provided on a side wall of the casing of the electronic cassette 26.

When the charging function of the battery 60 housed in the electronic cassette 26 is low, or when there is not enough time to charge the battery 60, an AC adapter is connected to the input terminal 296 in order to supply electric power from an external source, thereby making the electronic cassette 26 immediately operable.

The USB terminal 300 or the card slot 304 can be used at times when the electronic cassette 26 is unable to send and receive information by way of wireless communications to and from an external device such as the console 28 or the like. More specifically, when the USB memory 298 is inserted into the USB terminal 300, the electronic cassette 26 can send and receive information to and from the external device by recording necessary information in the USB memory 298, whereupon the USB memory 298 then is removed and inserted into the external device. Alternatively, the memory card 302 is inserted into the card slot 304 and necessary information from the electronic cassette 26 is recorded into the memory card 302. Thereafter, the memory card 302 is disconnected from the electronic cassette 26 and connected to the external device in order to send the information to the external device.

Figure 17:
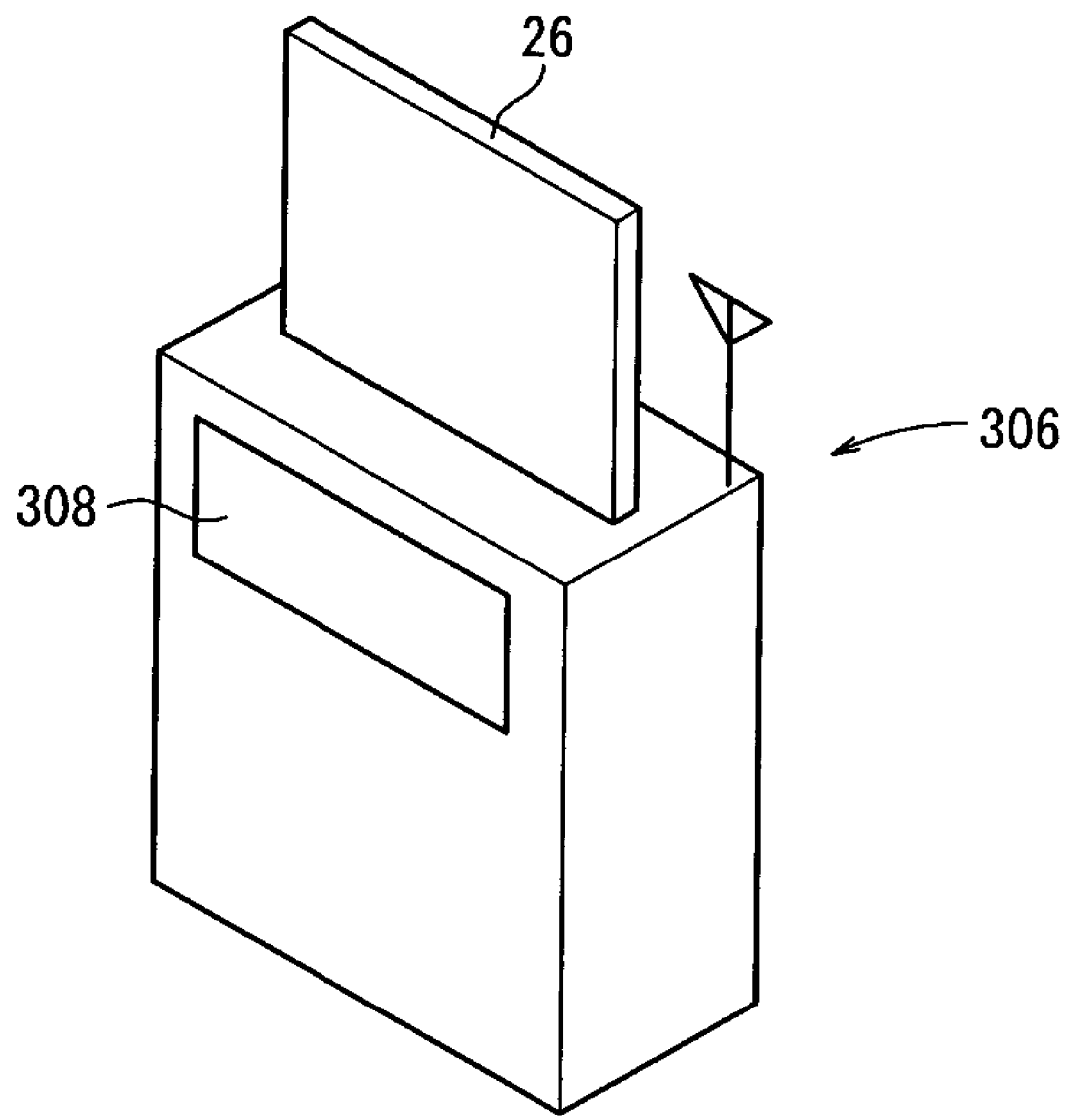
FIG. 17 is a perspective view of a cradle for charging a battery in the electronic cassette.

FIG. 17 shows a cradle 306 for receiving the electronic cassette 26 and charging the battery 60 housed in the electronic cassette 26. The cradle 306 is positioned in the radiographic image capturing chamber 22, or at any desired location in the hospital. The cradle 306 is not only capable of charging the battery 60, but may also have a wireless or wired communications function capable of sending and receiving necessary information to and from the console 28 or to the remote manager 20 via the LAN 18, rather than using the transceiver terminal 64, for the purpose of saving power stored in the battery 60. Information that is sent from the cradle 306 may include radiographic image information, offset image information, etc., recorded in the electronic cassette 26 that is loaded in the cradle 306.

The cradle 306 has a display unit 308 for displaying a charged state of the battery 60 housed in the electronic cassette 26, along with other necessary information including radiographic image information acquired from the electronic cassette 26.

A plurality of cradles 306 may be connected to the LAN 18, whereby charged states of the batteries 60 housed in the electronic cassettes 26 that are loaded in the respective cradles 306 may be retrieved through the LAN 18. Thus, based on the retrieved charged states of the batteries 60, the user can confirm locations of electronic cassettes 26 having batteries 60 that are sufficiently charged.

Although certain preferred embodiments of the present invention have been shown and described in detail, it should be understood that various changes and modifications may be made to the embodiments without departing from the scope of the invention as set forth in the appended claims.

What is claimed is:

1. A radiographic image capture managing system comprising:
   at least one radiographic image capturing system including a radiation source, a radiation detector for detecting radiation emitted from the radiation source and transmitted through a subject and converting the detected radiation into radiographic image information, and a controller for controlling at least the radiation source and the radiation detector; and
   a manager for managing the at least one radiographic image capturing system;
   the manager comprising:
   an information storage unit for storing at least one item of image information acquired by the radiation detector in chronological order;
   a usage status acquirer for acquiring information concerning a usage status of the radiation detector;
   a deterioration information acquirer for acquiring information concerning an extent of deterioration of the radiation detector based on the at least one item of image information stored in the information storage unit;
   a service life predictor for predicting a service life of the radiation detector based on the acquired information concerning the extent of deterioration of the radiation detector and the acquired information concerning the usage status of the radiation detector;
   a service life prolongation information setter for setting information concerning a new usage status required to prolong the predicted service life based on a preset relationship between the usage status and deterioration of the radiation detector and the acquired information concerning the usage status of the radiation detector; and
   a service life prolongation advice output unit for transmitting the information concerning the new usage status as service life prolongation advice information to at least the controller.

2. A radiographic image capture managing system according to claim 1, wherein the image information stored in the information storage unit comprises the radiographic image information.

3. A radiographic image capture managing system according to claim 1, wherein the manager further comprises:
   an offset image acquirer for reading a dark current of the radiation detector and acquiring offset image information from the read dark current,
   wherein the image information stored in the information storage unit comprises the offset image information.

4. A radiographic image capture managing system according to claim 1, wherein the information concerning the extent of deterioration of the radiation detector comprises at least a size (number of pixels) of a pixel defect.

5. A radiographic image capture managing system according to claim 4, wherein the information concerning the usage status comprises an environmental temperature of the radiation detector.

6. A radiographic image capture managing system according to claim 5, wherein the usage status acquirer acquires the information concerning the usage status of the radiation detector from a history of temperature information produced by a thermometer associated with the radiation detector.

7. A radiographic image capture managing system according to claim 4, wherein the information concerning the usage status comprises a dose of radiation applied to the radiation detector.

8. A radiographic image capture managing system according to claim 7, wherein the usage status acquirer acquires the information concerning the usage status of the radiation detector from a history of tube voltages set in the radiation source.

9. A radiographic image capture managing system according to claim 1, wherein a processing sequence is periodically performed over at least the usage status acquirer, the deterioration information acquirer, the service life predictor, the service life prolongation information setter, and the service life prolongation advice output unit.

10. A radiographic image capture managing system according to claim 1, wherein a processing sequence is periodically performed over at least the usage status acquirer, the deterioration information acquirer, and the service life predictor; and
    after the processing sequence is performed a plurality of times over the usage status acquirer, the deterioration information acquirer, and the service life predictor, the service life prolongation information setter and the service life prolongation advice output unit perform processes thereof.

11. A radiographic image capture managing system according to claim 1, wherein a processing sequence is periodically performed over at least the usage status acquirer, the deterioration information acquirer, and the service life predictor; and
    when a time representing the predicted service life falls within a threshold value, the service life prolongation information setter and the service life prolongation advice output unit perform processes thereof.

12. A radiographic image capture managing system according to claim 9, wherein the processing sequence is periodically performed at time intervals that are changed depending on the extent of deterioration of the radiation detector.

13. A radiographic image capture managing system according to claim 9, wherein the processing sequence is periodically performed at time intervals that are made shorter when a time representing the predicted service life falls within a threshold value.

14. A radiographic image capture managing method for managing at least one radiographic image capturing system including a radiation source, a radiation detector for detecting radiation emitted from the radiation source and transmitted through a subject and converting the detected radiation into radiographic image information, and a controller for controlling at least the radiation source and the radiation detector, comprising the steps of:

storing at least one item of image information acquired by the radiation detector in an information storage unit in chronological order;

acquiring information concerning a usage status of the radiation detector;

acquiring information concerning an extent of deterioration of the radiation detector based on the at least one item of image information stored in the information storage unit;

predicting a service life of the radiation detector based on the acquired information concerning the extent of deterioration of the radiation detector and the acquired information concerning the usage status of the radiation detector;

setting information concerning a new usage status required to prolong the predicted service life based on a preset relationship between the usage status and deterioration of the radiation detector and the acquired information concerning the usage status of the radiation detector; and transmitting the information concerning the new usage status as service life prolongation advice information to at least the controller.

* * * * *